(12) United States Patent
Gittings et al.

(10) Patent No.: US 7,025,773 B2
(45) Date of Patent: Apr. 11, 2006

(54) METHODS AND DEVICES FOR PLACING A CONDUIT IN FLUID COMMUNICATION WITH A TARGET VESSEL

(75) Inventors: Darin C. Gittings, Sunnyvale, CA (US); Alan R. Rapacki, Redwood City, CA (US); Dean F. Carson, Mountain View, CA (US); David H. Cole, Cupertino, CA (US); Keke Lepulu, Redwood City, CA (US); Adam Sharkawy, Redwood City, CA (US); Gilbert S. Laroya, Santa Clara, CA (US); Wally S. Buch, Atherton, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/850,883

(22) Filed: May 7, 2001

(65) Prior Publication Data
US 2002/0004663 A1 Jan. 10, 2002

Related U.S. Application Data

(63) Continuation of application No. 09/304,140, filed on May 3, 1999, now abandoned, which is a continuation-in-part of application No. 09/232,103, filed on Jan. 15, 1999, now abandoned, and a continuation-in-part of application No. 09/232,062, filed on Jan. 15, 1999, now abandoned.

(51) Int. Cl.
*A61B 17/08* (2006.01)

(52) U.S. Cl. ............................................. 606/153

(58) Field of Classification Search ................ 606/153, 606/151, 152, 159, 108, 156; 623/1.15–1.2
See application file for complete search history.

(56) References Cited

U.S. PATENT DOCUMENTS

| | | | |
|---|---|---|---|
| 2,127,903 | A | 8/1938 | Bowen |
| 2,453,056 | A | 11/1948 | Zack |
| 3,042,021 | A | 7/1962 | Read |

(Continued)

FOREIGN PATENT DOCUMENTS

| GB | 2316322 | 2/1998 |
|---|---|---|

(Continued)

OTHER PUBLICATIONS

JOMED Direction, product literature, no date.

*Primary Examiner*—Howard Weiss
*Assistant Examiner*—Hoa (Vikki) B. Trinh
(74) *Attorney, Agent, or Firm*—Tom Berry; Jeffrey J. Hohenshell

(57) ABSTRACT

Methods and devices for placing a conduit in fluid communication with a target vessel and a source of blood, such as the aorta or a heart chamber. The device may be actuated using one hand to place the conduit. The invention allows air in the conduit to be removed prior to placement of the conduit. The invention deploys the conduit in the target vessel by moving a sheath in a distal direction and then in a proximal direction. A conduit is provided with a reinforcing member to prevent kinking of the conduit, and a structure for preventing blockage of the conduit by tissue. A vessel coupling may be used to secure a conduit to a target vessel so as to preserve native blood flow through the vessel, and the conduit may be placed in fluid communication with a target vessel via a laparoscopic or endoscopic procedure.

6 Claims, 20 Drawing Sheets

U.S. PATENT DOCUMENTS

| | | | |
|---|---|---|---|
| 3,316,914 | A | 5/1967 | Collito |
| 3,540,451 | A | 11/1970 | Zeman |
| 3,774,615 | A | 11/1973 | Lim et al. |
| 3,995,617 | A | 12/1976 | Watkins et al. |
| 4,300,244 | A | 11/1981 | Brokos |
| 4,368,736 | A | 1/1983 | Kaster |
| 4,400,833 | A | 8/1983 | Kurland |
| 4,523,592 | A | 6/1985 | Daniel |
| 4,546,499 | A | 10/1985 | Possis et al. |
| 4,562,597 | A | 1/1986 | Possis et al. |
| 4,581,017 | A | 4/1986 | Sahota et al. |
| 4,712,551 | A | 12/1987 | Rayhanabad |
| 4,728,328 | A | 3/1988 | Hughes |
| 4,769,029 | A | 9/1988 | Patel |
| 4,769,031 | A | 9/1988 | McGough et al. |
| 4,861,330 | A | 8/1989 | Vos |
| 4,862,886 | A | 9/1989 | Clark et al. |
| 4,902,289 | A | 2/1990 | Yannes |
| 4,953,553 | A | 9/1990 | Tremulis |
| 4,955,856 | A | 9/1990 | Philips |
| 4,955,899 | A | 9/1990 | Della Corna et al. |
| 4,985,014 | A | 1/1991 | Orejola |
| 4,995,857 | A | 2/1991 | Arnold |
| 5,054,484 | A | 10/1991 | Hebeler, Jr. |
| 5,071,406 | A | 12/1991 | Jang |
| 5,078,735 | A | 1/1992 | Mobin-Uddin |
| 5,100,423 | A | 3/1992 | Fearnot |
| 5,106,386 | A | 4/1992 | Isner et al. |
| 5,111,832 | A | 5/1992 | Sakesena |
| 5,143,093 | A | 9/1992 | Sahota |
| 5,190,058 | A | 3/1993 | Jones et al. |
| 5,209,731 | A | 5/1993 | Sterman et al. |
| 5,211,624 | A | 5/1993 | Cinberg et al. |
| 5,250,058 | A | 10/1993 | Miller et al. |
| 5,254,097 | A | 10/1993 | Schock et al. |
| 5,254,113 | A | 10/1993 | Wilk |
| 5,256,150 | A | 10/1993 | Quiachon et al. |
| 5,275,622 | A | 1/1994 | Lazarus et al. |
| 5,287,861 | A | 2/1994 | Wilk |
| 5,314,436 | A | 5/1994 | Wilk |
| 5,327,913 | A | 7/1994 | Taheri |
| 5,330,500 | A | 7/1994 | Song |
| 5,370,685 | A | 12/1994 | Stevens |
| 5,380,316 | A | 1/1995 | Aita et al. |
| 5,383,892 | A | 1/1995 | Cardon et al. |
| 5,383,925 | A | 1/1995 | Schmitt |
| 5,389,096 | A | 2/1995 | Aita et al. |
| 5,395,349 | A | 3/1995 | Quiachon et al. |
| 5,397,320 | A | 3/1995 | Essig et al. |
| 5,409,019 | A | 4/1995 | Wilk |
| 5,425,705 | A | 6/1995 | Evard et al. |
| 5,425,765 | A | 6/1995 | Tiefenbrun et al. |
| 5,429,144 | A | 7/1995 | Wilk |
| 5,443,497 | A | 8/1995 | Venbrux |
| 5,452,733 | A | 9/1995 | Sterman et al. |
| 5,456,714 | A | 10/1995 | Owen |
| 5,458,574 | A | 10/1995 | Machold et al. |
| 5,466,242 | A | 11/1995 | Mori |
| 5,484,418 | A | 1/1996 | Quiachon et al. |
| 5,489,295 | A | 2/1996 | Piplani et al. |
| 5,494,041 | A | 2/1996 | Wilk |
| 5,501,698 | A | 3/1996 | Roth et al. |
| 5,503,635 | A | 4/1996 | Sauer et al. |
| 5,505,725 | A | 4/1996 | Samson |
| 5,522,880 | A | 6/1996 | Barone et al. |
| 5,549,581 | A | 8/1996 | Lurie et al. |
| 5,591,226 | A | 1/1997 | Trerotola et al. |
| 5,603,722 | A | 2/1997 | Phan et al. |
| 5,620,439 | A | 4/1997 | Abela et al. |
| 5,653,743 | A | 8/1997 | Martin |
| 5,655,548 | A | 8/1997 | Nelson et al. |
| 5,662,124 | A | 9/1997 | Wilk |
| 5,695,504 | A | 12/1997 | Gifford, III et al. |
| 5,697,943 | A | 12/1997 | Sauer et al. |
| 5,702,412 | A | 12/1997 | Popov et al. |
| 5,755,682 | A | 5/1998 | Knudson et al. |
| 5,755,778 | A | 5/1998 | Kleshinski |
| 5,758,663 | A | 6/1998 | Wilk et al. |
| 5,799,661 | A * | 9/1998 | Boyd et al. ................ 128/898 |
| 5,810,836 | A | 9/1998 | Hussein et al. |
| 5,814,005 | A | 9/1998 | Barra et al. |
| 5,817,113 | A | 10/1998 | Gifford, III et al. |
| 5,824,042 | A | 10/1998 | Lombardi et al. |
| 5,824,071 | A | 10/1998 | Nelson et al. |
| 5,830,222 | A | 11/1998 | Makower |
| 5,830,224 | A | 11/1998 | Cohn et al. |
| 5,836,316 | A | 11/1998 | Plaia et al. |
| 5,843,088 | A | 12/1998 | Barra et al. |
| 5,843,165 | A | 12/1998 | Plaia et al. |
| 5,855,597 | A | 1/1999 | Jayaraman |
| 5,871,536 | A | 2/1999 | Lazarus |
| 5,875,782 | A | 3/1999 | Ferrari et al. |
| 5,879,321 | A | 3/1999 | Hill |
| 5,888,201 | A | 3/1999 | Stinson et al. |
| 5,888,247 | A | 3/1999 | Benetti |
| 5,893,369 | A | 4/1999 | LeMole |
| 5,893,886 | A | 4/1999 | Zegdi et al. |
| 5,895,407 | A | 4/1999 | Jayaraman |
| 5,897,587 | A | 4/1999 | Martakos et al. |
| 5,897,589 | A | 4/1999 | Cottenceau et al. |
| 5,899,934 | A | 5/1999 | Amundson et al. |
| 5,904,697 | A | 5/1999 | Gifford et al. |
| 5,908,028 | A | 6/1999 | Wilk |
| 5,908,029 | A | 6/1999 | Knudson et al. |
| 5,910,168 | A | 6/1999 | Myers et al. |
| 5,911,753 | A | 6/1999 | Schmitt |
| 5,913,894 | A | 6/1999 | Schmitt |
| 5,916,226 | A | 6/1999 | Tozzi |
| 5,916,264 | A | 6/1999 | Von Oepen et al. |
| 5,925,033 | A | 7/1999 | Aita et al. |
| 5,941,893 | A | 8/1999 | Saadat |
| 5,941,908 | A | 8/1999 | Goldsteen et al. |
| 5,944,019 | A | 8/1999 | Knudson et al. |
| 5,971,993 | A | 10/1999 | Hussein et al. |
| 5,972,017 | A * | 10/1999 | Berg et al. ................ 606/198 |
| 5,976,178 | A | 11/1999 | Goldsteen et al. |
| 5,980,567 | A | 11/1999 | Jordan |
| 5,984,956 | A | 11/1999 | Tweden et al. |
| 5,989,276 | A | 11/1999 | Houser et al. |
| 5,989,287 | A | 11/1999 | Yang et al. |
| 5,993,489 | A | 11/1999 | Lewis et al. |
| 6,001,124 | A | 12/1999 | Bachinski |
| 6,007,576 | A | 12/1999 | McClellan |
| 6,035,856 | A | 3/2000 | LaFontaine et al. |
| 6,074,416 | A | 6/2000 | Berg et al. |
| 6,092,526 | A | 7/2000 | LaFontaine et al. |
| 6,113,612 | A | 9/2000 | Swanson et al. |
| 6,143,016 | A * | 11/2000 | Bleam et al. ............... 606/198 |
| 6,165,185 | A | 12/2000 | Shennib et al. |
| 6,176,864 | B1 | 1/2001 | Chapman |
| 6,190,397 | B1 | 2/2001 | Spence et al. |
| 6,231,587 | B1 | 5/2001 | Makower |
| 6,241,741 | B1 | 6/2001 | Duhaylongsod et al. |
| 6,253,769 | B1 | 7/2001 | LaFontaine et al. |
| 6,352,543 | B1 | 3/2002 | Cole |
| 6,517,558 | B1 * | 2/2003 | Gittings et al. ............. 606/153 |
| 6,635,214 | B1 | 10/2003 | Rapacki et al. |
| 6,651,670 | B1 | 11/2003 | Rapacki et al. |
| 6,652,540 | B1 * | 11/2003 | Cole et al. ................ 606/153 |
| 6,719,768 | B1 | 4/2004 | Cole et al. |

FOREIGN PATENT DOCUMENTS

| | | |
|---|---|---|
| WO | WO 88/06865 | 9/1988 |

| | | |
|---|---|---|
| WO | WO 96/22745 | 8/1996 |
| WO | WO 97/12555 | 4/1997 |
| WO | WO 98/16174 | 4/1998 |
| WO | WO 98/19629 | 5/1998 |
| WO | WO 98/19630 | 5/1998 |
| WO | WO 98/38939 | 9/1998 |
| WO | WO 98/38941 | 9/1998 |
| WO | WO 98/38942 | 9/1998 |
| WO | WO 98/57590 | 12/1998 |
| WO | WO 98/57592 | 12/1998 |
| WO | WO 99/18887 | 4/1999 |
| WO | WO 99/36001 | 7/1999 |
| WO | WO 99/38459 | 8/1999 |
| WO | WO 99/53863 | 10/1999 |
| WO | WO 99/63910 | 12/1999 |
| WO | WO 99/65409 | 12/1999 |
| WO | WO 00/69364 | 11/2000 |
| WO | WO 00/74579 | 12/2000 |
| WO | WO 01/39672 | 6/2001 |

* cited by examiner

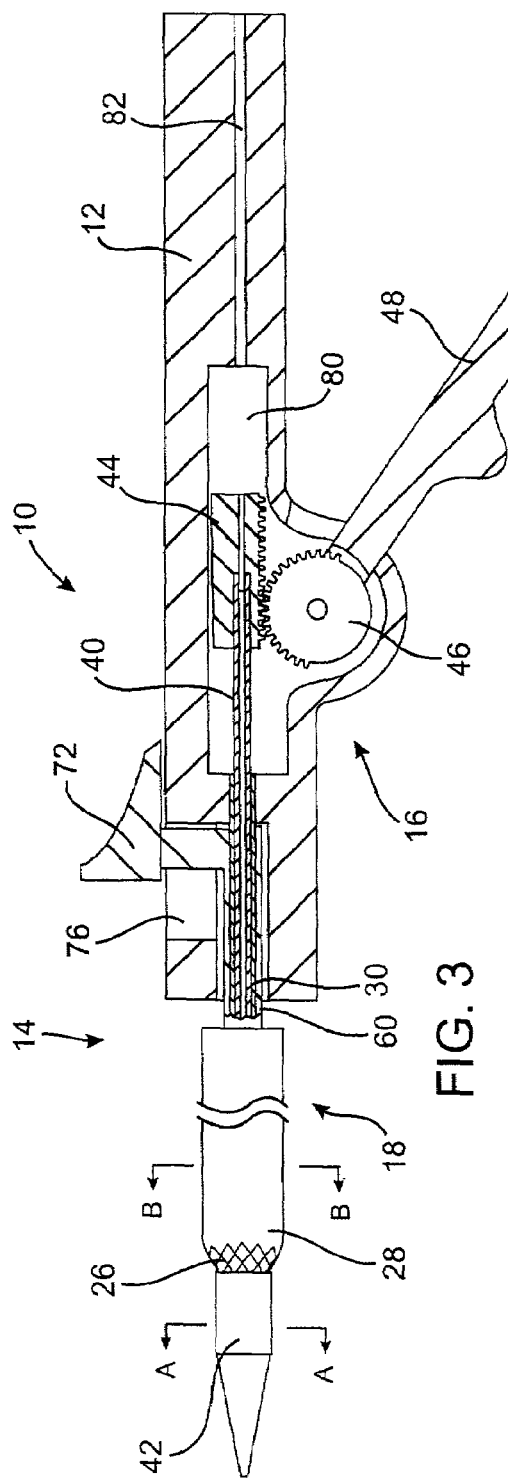
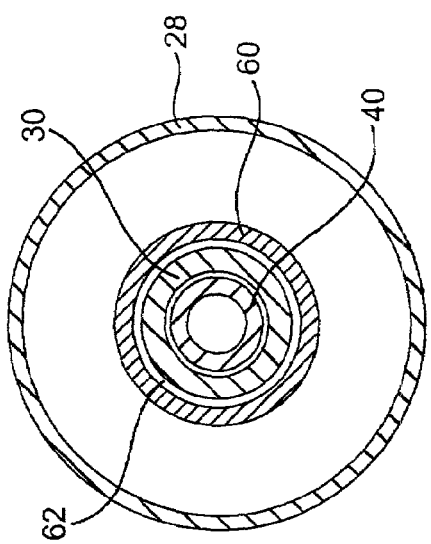
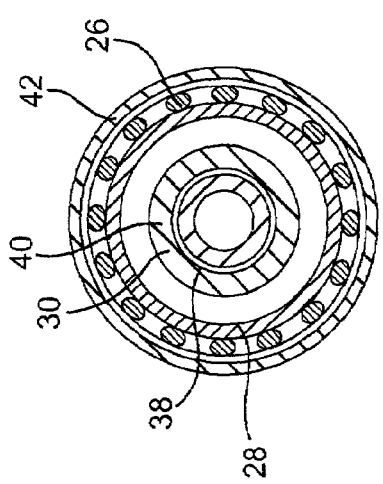
FIG. 3
FIG. 3A
FIG. 3B

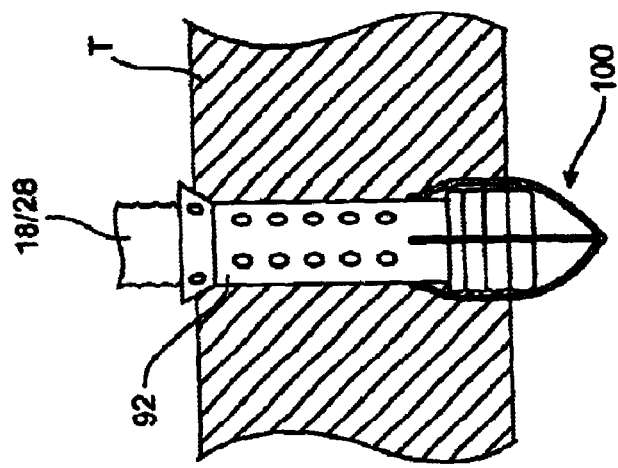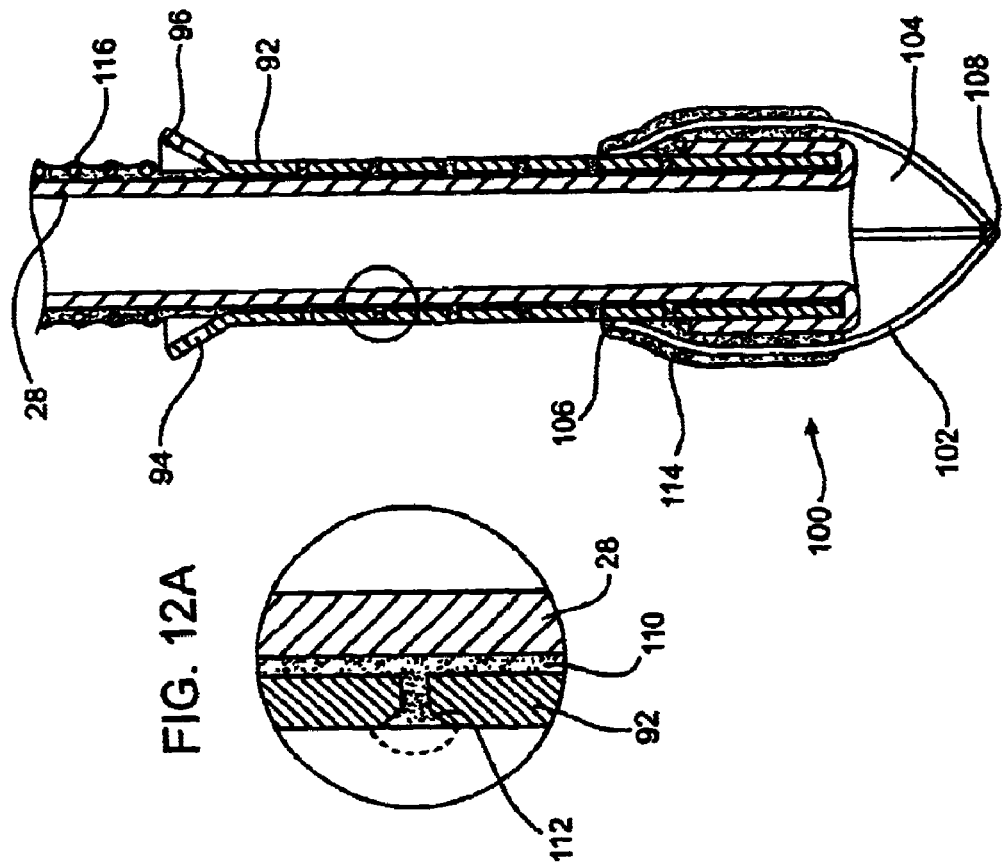

METHODS AND DEVICES FOR PLACING A CONDUIT IN FLUID COMMUNICATION WITH A TARGET VESSEL

CROSS-REFERENCE TO RELATED APPLICATIONS

This application is a continuation of U.S. patent application Ser. No. 09/304,140, filed May 3, 1999 now abandoned, which is a continuation-in-part of application Ser. No. 09/232,103, filed on Jan. 15, 1999 now abandoned and entitled "Methods and Devices for Forming Vascular Anastomoses," the entire subject matter of which is incorporated herein by reference. This application is also a continuation-in-part of application Ser. No. 09/232,062, filed on Jan. 15, 1999 now abandoned and entitled "Methods and Devices For Bypassing an Obstructed Target Vessel by Placing the Vessel in Communication with a Heart Chamber Containing Blood," the entire subject matter of which is also incorporated herein by reference.

BACKGROUND OF THE INVENTION

1. Field of the Invention

The invention relates to methods and devices for placing a conduit in fluid communication with a lumen of a target vessel, and more particularly methods and devices for placing such a conduit in-fluid communication with a target vessel and a source of blood.

2. Description of the Related Art

Despite the considerable advances that have been realized in cardiology and cardiovascular surgery, heart disease remains the leading cause of death throughout much of the world. Coronary artery disease, or arteriosclerosis, is the single leading cause of death in the United States today. As a result, those in the cardiovascular field continue to search for new and improved treatments.

Coronary artery disease is currently treated by interventional procedures such as percutaneous transluminal coronary angioplasty (PTCA), atherectomy and coronary stenting, as well as surgical procedures including coronary artery bypass grafting (CABG). The goal of these procedures is to reestablish or improve blood flow through occluded (or partially occluded) coronary arteries, and is accomplished, for example, by enlarging the blood flow lumen of the artery or forming a bypass that allows blood to circumvent the occlusion. What procedure(s) is used typically depends on the severity and location of the blockages. When successful, these procedures restore blood flow to myocardial tissue that had not been sufficiently perfused due to the occlusion.

Another treatment that has been recently proposed places the target vessel in fluid communication with a heart chamber, for example, the left ventricle. The target vessel and the heart chamber may be communicated by a conduit passing through the myocardium. Some of the challenges associated with such procedures include proper positioning of the conduit in the myocardium as well as correct placement of the conduit in a coronary artery.

As shown by these and other attempts to develop new and improved treatments that may be used to deliver blood to myocardial tissue, there remains a need in the art for methods and devices that may be used to place a conduit in fluid communication with a target vessel and a source of blood.

SUMMARY OF THE INVENTION

According to one embodiment of the invention, methods and devices are provided for placing a conduit in fluid communication with a target vessel. One preferred method includes steps of providing a conduit having a first end, a second end and a lumen, the conduit being supported by a conduit delivery device. A portion of the device is positioned adjacent a target vessel in a patient's vascular system, one of the first and second ends of the conduit is placed in fluid communication with the target vessel, and the conduit is removed from the delivery device. The steps of positioning the portion of the conduit delivery device adjacent the target vessel and placing one of the first and second ends of the conduit in fluid communication with the target vessel are performed using one hand.

One preferred device includes a conduit having a first end, a second end and a lumen, wherein the conduit is movable between deployed and non-deployed positions and one end of the conduit is adapted to be placed in fluid communication with a target vessel. A sheath overlies at least a portion of the conduit and holds the portion in the non-deployed position. A first actuator imparts relative movement to the conduit and the sheath in order to allow the portion of the conduit to move to the deployed position. A sheath removal mechanism is provided for removing the sheath after the conduit has moved to the deployed position. The first actuator and the sheath removal mechanism are operable using one hand to place the conduit in fluid communication with the target vessel and remove the sheath from the target vessel.

According to another embodiment of the invention, methods and devices are provided for placing a conduit in fluid communication with a target vessel and a source of blood. One preferred method includes steps of providing a conduit having a first end, a second end and a lumen, placing the first end of the conduit in fluid communication with the source of blood, allowing blood to flow into the lumen of the conduit to force substantially all air from the conduit, and placing the second end of the conduit in fluid communication with the target vessel.

One preferred device includes a conduit having a first end, a second end and a lumen, wherein the first end of the conduit is adapted to be placed in fluid communication with a target vessel and the second end of the conduit is adapted to be placed in communication with a source of blood. A support shaft has a section that is removably coupled to the first end of the conduit for placing the first end of the conduit in fluid communication with the target vessel, but decoupled from the second end of the conduit to allow the second end of the conduit to be placed in communication with the source of blood prior to placing the first end of the conduit in fluid communication with the target vessel.

According to another embodiment of the invention, methods and devices are provided for establishing a conduit to place a coronary vessel in fluid communication with a heart chamber containing oxygenated blood. One preferred method includes steps of placing a conduit in fluid communication with a heart chamber containing oxygenated blood, wherein at least a major portion of the length of the conduit is disposed exterior to the heart wall. The conduit is also placed in fluid communication with a lumen of a coronary vessel, and is secured to the coronary vessel by a sutured anastomosis so as to place the coronary vessel in fluid communication with the heart chamber.

According to another embodiment of the invention, methods and devices are provided for deploying a conduit in a target vessel. One preferred method includes steps of providing a conduit having a first end, a second end and a lumen, wherein the conduit is movable between deployed and non-deployed positions and at least a portion of the conduit is held in the non-deployed position by a retention member. At least the non-deployed portion of the conduit is placed in a lumen of a target vessel, and the retention member is moved in a first direction with respect to the conduit to move the non-deployed portion of the conduit to the deployed position. The retention member is moved in a second direction that is substantially opposite the first direction to remove the retention member from the target vessel.

One preferred device includes a conduit having a first end, a second end and a lumen, wherein the conduit is movable between deployed and non-deployed positions and one end of the conduit is adapted to be placed in fluid communication with a target vessel. A retention member overlies at least a portion of the conduit to hold the portion in the non-deployed position. An actuator is coupled to the retention member and is moved in a first direction to move the retention member and allow the portion of the conduit to move to the deployed position. The actuator is then moved in a second direction to remove the retention member from the target vessel, the second direction being transverse to the first direction.

According to another embodiment of the invention, methods and devices are provided for placing a conduit in fluid communication with a target vessel while preserving native blood flow through the target vessel. One preferred method includes steps of providing a vessel coupling and a conduit, wherein the vessel coupling has a first portion configured to secure the conduit to a target vessel so that the conduit is in fluid communication with the target vessel. The vessel coupling is moved generally along a first direction to place the first portion of the vessel coupling at least partially within the lumen of the target vessel, and the first portion of the vessel coupling is then moved generally along a second direction within the lumen of the target vessel to deploy the vessel coupling and secure the conduit to the target vessel, wherein the second direction is transverse to the first direction.

One preferred device includes a vessel coupling including a first portion joined to a second portion, wherein the first portion of the vessel coupling is sized and configured to be attached to a target vessel while allowing native blood flow through the target vessel to move past the site of attachment. The second portion of the vessel coupling is sized and configured to be coupled to a conduit that is adapted to form a flow path between the target vessel and a source of blood. The first portion of the vessel coupling includes a plurality of support members sized and configured to engage a wall of the target vessel, each support member including a plurality of generally straight support struts.

According to another embodiment of the invention, methods and devices are provided for forming a blood flow path through tissue. One preferred device includes a tubular member having a first end, a second end and a lumen, wherein the tubular member is configured to be placed in tissue and the lumen of the tubular member is sized and configured to receive a conduit adapted to form a blood flow path through the tissue. At least one of the first and second ends of the tubular member is configured to extend through the tissue so as to place the conduit in fluid communication with a hollow body structure containing blood, and a structure is coupled to the one end of the tubular member for maintaining the one end substantially open. The structure includes at least one opening through which blood from the hollow body structure may enter the conduit.

According to another embodiment of the invention, methods and devices are provided for placing a conduit in fluid communication with a target vessel in a patient's vascular system by passing a device through a port located between adjacent ribs. One preferred method includes steps of providing a conduit having a first end, a second end and a lumen, wherein the conduit is supported by a conduit delivery device having a portion that is sized and configured to be passed through a port located between adjacent ribs in a patient's body, and passing the portion of the conduit delivery device through the port to a location adjacent the target vessel. One of the first and second ends of the conduit is placed in fluid communication with a lumen of the target vessel, the conduit is removed from the conduit delivery device, and the conduit delivery device is removed from the port.

BRIEF DESCRIPTION OF THE DRAWING FIGURES

Various other aspects, features, benefits and advantages of the invention will be better understood from the following detailed description of preferred embodiments thereof, taken in conjunction with the accompanying drawing figures, wherein:

FIG. 3 is a longitudinal sectional view of the device shown in FIG. 1;

FIGS. 3A and 3B are transverse sectional views taken, respectively, along lines A—A and B—B in FIG. 3;

FIG. 11 is a sectional view illustrating the end of the conduit shown in FIG. 9 placed in the myocardium;

FIG. 12 is a sectional view of a portion of a conduit constructed according to another embodiment of the invention, wherein the end of the conduit is configured for placement in the myocardium;

FIG. 12A is an enlarged view of the portion encircled in FIG. 12;

DETAILED DESCRIPTION OF PREFERRED EMBODIMENTS

Figure 1:
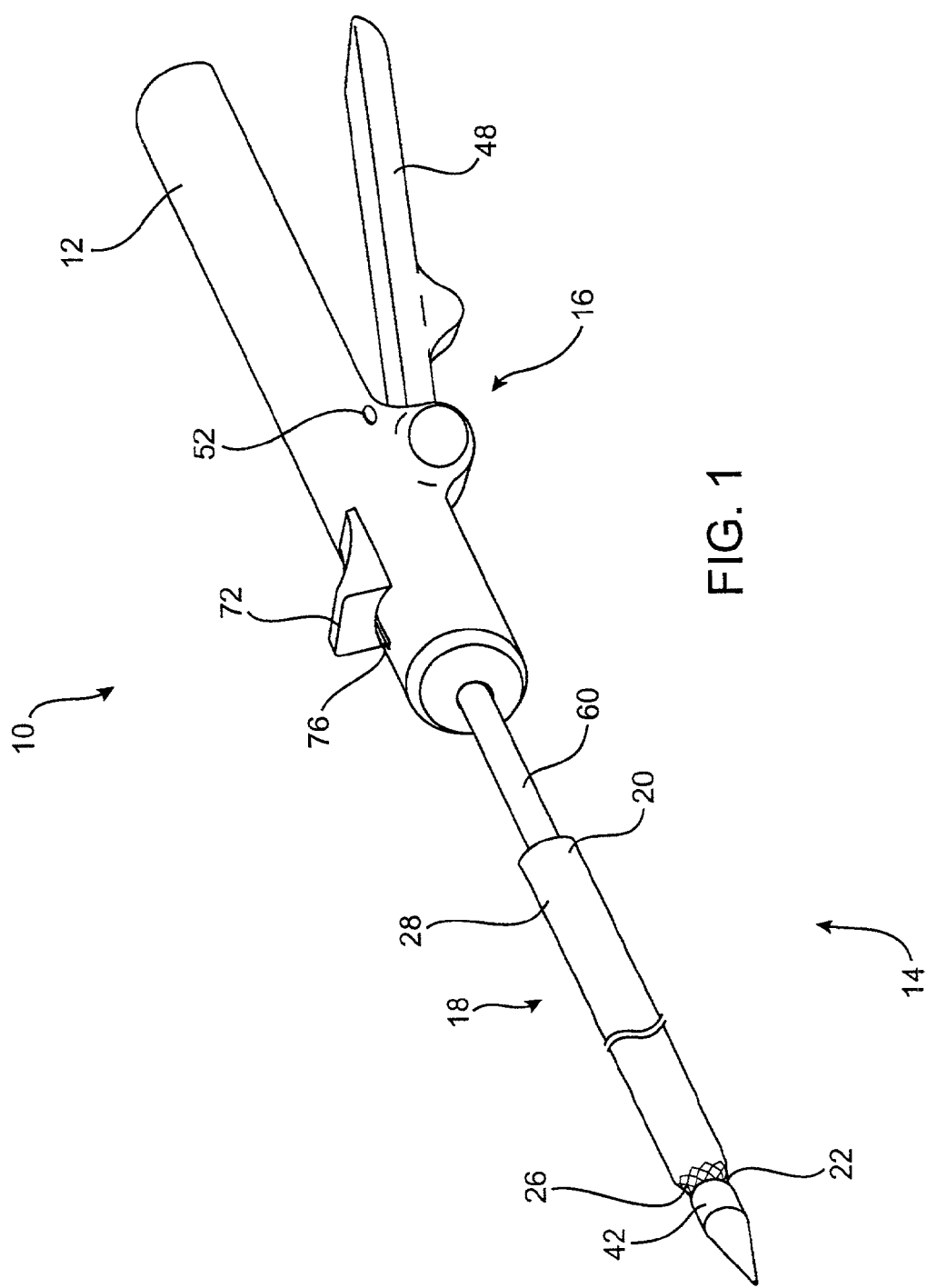
FIG. 1 is a perspective view of a device constructed according to one embodiment of the invention for placing a conduit in fluid communication with a target vessel.

Referring to FIGS. 1–4, a device constructed according to one preferred embodiment of the invention is indicated generally by the reference numeral 10. The device 10 is used to place a conduit in fluid communication with a target vessel, the conduit also preferably being placed in fluid communication with a source of blood. As used herein, source of blood refers to any structure containing blood, although a structure containing oxygenated blood, i.e., blood containing some level of oxygen, is preferred. For example, the source of blood may be a heart chamber while the target vessel may be a coronary artery or vein or another vessel.

Figure 2:
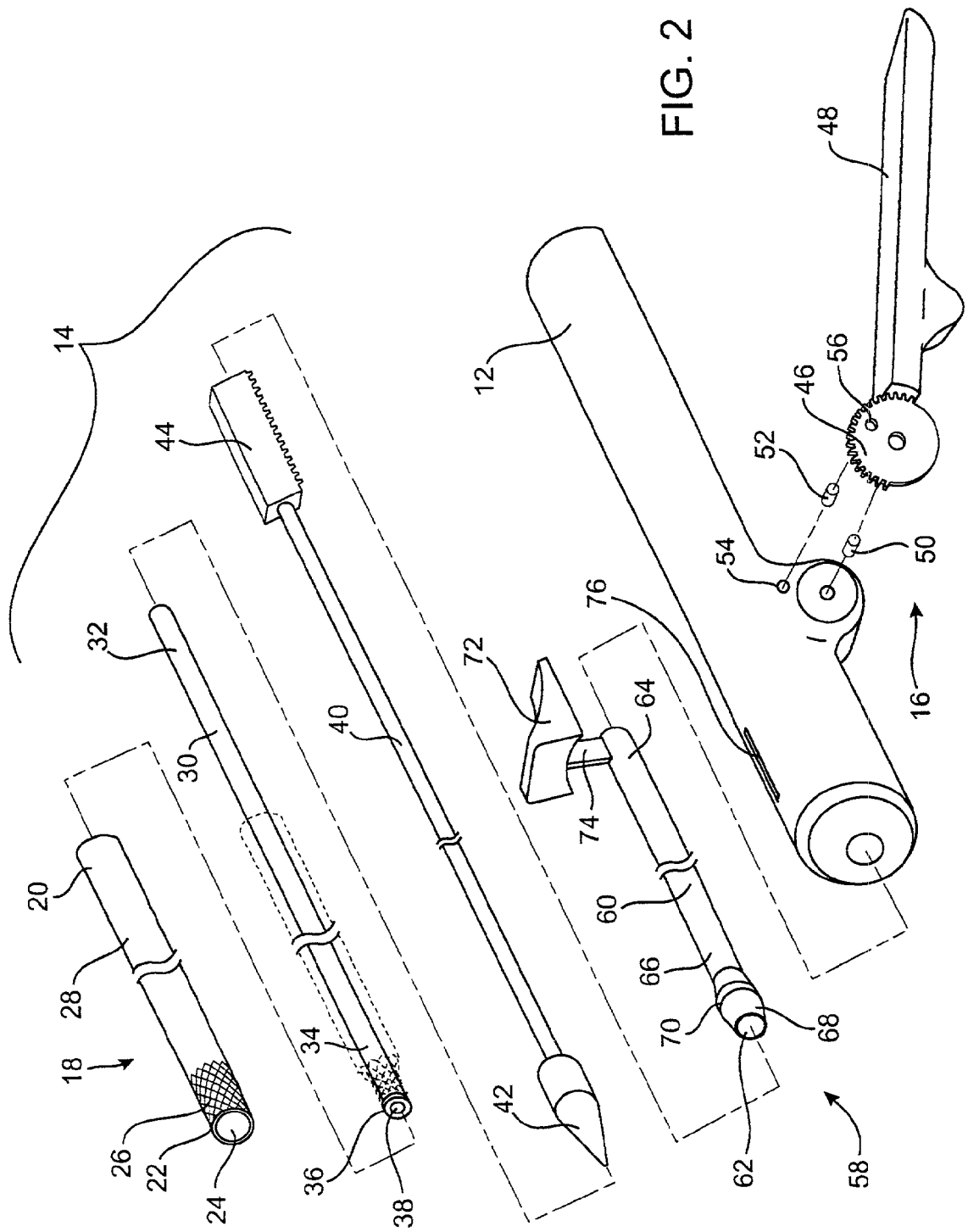
FIG. 2 is an exploded perspective view of the device shown in FIG. 1.
Figure 4:
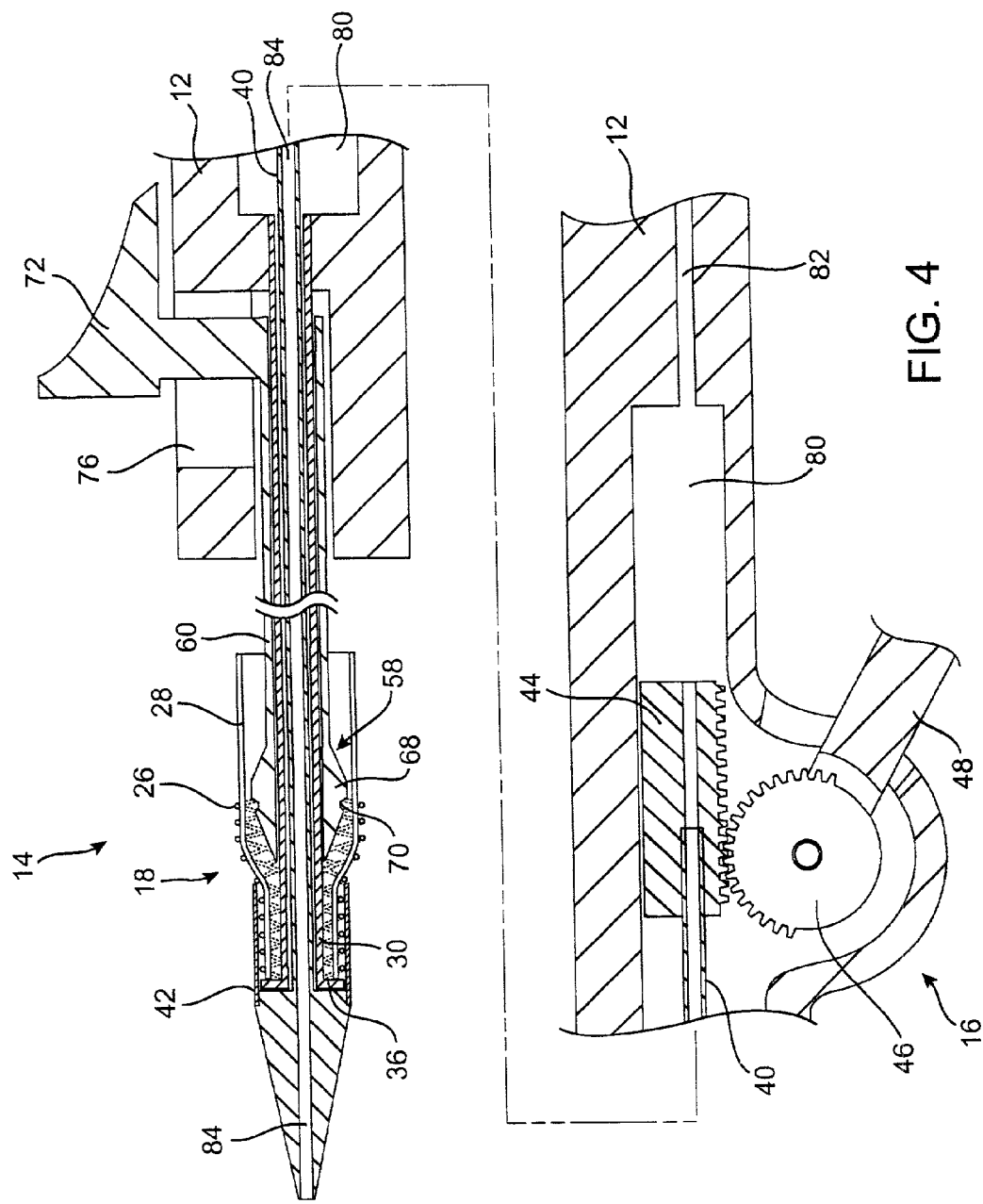
FIG. 4 is an enlarged, fragmentary longitudinal sectional view of the device shown in FIGS. 1 and 3.

The device 10 comprises a handle 12, a shaft assembly 14 and an actuator assembly 16 (FIGS. 2–4). The shaft assembly 14 may be relatively flexible to permit it to bend during use, or it may be substantially rigid. The degree of flexibility imparted to the shaft assembly 14 of the device 10, as well as the dimensions and shape of the device 10, may vary depending on the particular application and user preference.

The device 10 could be formed with a shaft assembly 14 that is curved, malleable or bendable to a selected configuration, or articulated with a movable portion that may be controlled or steered by known mechanisms, for example, mechanisms used to steer catheters or guide wires. As an example, the device could have a curved shaft assembly constructed according to the teachings in co-pending, commonly-owned application Ser. No. 09/304,141, filed on May 3, 1999 and entitled "Methods and Devices for Forming a Conduit Between a Target Vessel and a Blood Source," the entire subject matter of which is hereby incorporated by reference.

The application of the invention illustrated in the Figures places a conduit in fluid communication with a target vessel and a source of blood. The term conduit refers to a flow path established between the target vessel and the blood source and includes structure that defines (either partially or completely) the flow path. A conduit constructed according to the invention may comprise one or more sections, each of which sections may comprise various materials. It will be appreciated that the specific conduit configurations illustrated in connection with preferred embodiments described herein is for sake of example and is not intended to limit the scope or application of the invention.

The illustrated conduit 18 includes a proximal end 20, a distal end 22 and a lumen 24. The conduit 18 is deployed in a target vessel and preferably includes a vessel coupling that is configured to be secured to the target vessel. It should be understood, however, that the invention may be practiced without using a vessel coupling, for example, by securing the conduit to the target vessel with a sutured anastomosis created by hand or an automated suturing device, biologically compatible adhesives, fasteners, etc. A vessel coupling is preferred, however, to facilitate relatively easy and rapid attachment of the conduit to the target vessel as compared to creating a hand-sewn anastomosis. Also, the conduit may comprise tissue, synthetic vascular graft material, or a combination of tissue and synthetic vascular graft material. Thus, in a basic embodiment, the invention could comprise a tissue or synthetic conduit that is placed in communication with a source of blood such as the left ventricle, and hand-sutured to a target vessel such as a coronary artery.

In the illustrated embodiments, the conduit 18 comprises a length of synthetic vascular graft material, such as ePTFE, PTFE or Dacron, or another material that may be used to form a conduit that conveys blood, for example, silicone, PVA or polyurethane. The proximal end 20 of the conduit 18 is adapted to be placed in fluid communication with a source of blood (not shown in FIGS. 1–4) and for that purpose may include means for securing the conduit in place with respect to the blood source, such as a device configured to be implanted and fixed in tissue located adjacent the blood source. Alternatively, the proximal end 20 of the conduit 18 could be secured to tissue by other means, for example, any of the aforementioned means for securing the distal end of the conduit 18 to the target vessel.

In the most preferred embodiment, the conduit is secured to the target vessel by a substantially suture-free attachment, which means that the attachment is not a conventional hand-sewn anastomosis created by suturing the members together. As such, although some suture may be used in the preferred embodiment, the vessel coupling is attached to the target vessel by means other than a typical, hand-sewn sutured connection. The invention, however, may be practiced using suture as the means for attaching a conduit comprising tissue or synthetic vascular graft material to a target vessel.

The conduit 18 includes a vessel coupling that attaches the conduit to the target vessel, the vessel coupling preferably being expandable so that it may be collapsed for introduction into the vessel and then expanded against the vessel wall. It will be understood, however, that the invention may be practiced with a non-expandable vessel coupling, such as a rigid tubular member securely engaged with the wall of the target vessel, for example, by first dilating the vessel wall to place the element and then allowing the vessel wall to move back and snugly engage the exterior of the element.

The expandable vessel coupling moves between collapsed and expanded orientations and in the preferred embodiment comprises a stent 26. The stent 26 could be formed of various materials including nitinol, stainless steel, tantalum or titanium. As an example, the stent 26 may be a self-expanding nitinol stent joined to a liner or layer 28 of teflon (PTFE) or expanded teflon (ePTFE) to form the conduit 18. The stent 26 preferably includes a plurality of struts that permit the stent to collapse and expand, although other stent constructions may be used; for example, the stent could be wire-formed or could comprise a flat sheet of material that is unrolled to an expanded orientation.

As an example, the stent may be formed by subjecting a tube of suitable material to any of various procedures such as laser cutting, EDM (electrical discharge machining), photochemical etching, etc. The stent/tube material is preferably nitinol, but may be titanium, tantalum, etc. It may be desirable to further process or finish the cut stent to remove burrs or surface irregularities, for example, by acid etching, electropolishing, or abrasive blasting. The stent may then be placed in its collapsed orientation by cooling (e.g., with liquid nitrogen), coupled to a liner and loaded onto a delivery device, and then deployed in a target vessel. The liner of the conduit, for example, may comprise ePTFE having an inner diameter within the range of from about 1 mm to about 5 mm, and more preferably about 2 mm to about 4 mm, a wall thickness of about 0.2 mm, and an internodal distance or pore size in the range of from about 20 µs to about 100 µs.

The liner 28 is secured to the stent 26 by any suitable means, for example, one or more lengths of suture (not shown) that pass through the liner wall and the wall of the stent. Other suitable means for securing the two components include biologically compatible adhesives, ultrasonic welding, clips or fasteners, weaving the liner through the stent elements, tying the liner to the stent elements, etc. As shown in FIG. 2, the stent 26 is preferably aligned so as to extend a desired amount along part of the distal end 22 of the conduit 18. This relative position is preferred as it allows part of the stent 26 to extend through the wall of the target vessel when the conduit 18 has been deployed, this portion of the stent serving to hold the junction open to maintain fluid communication. However, it will be appreciated that the stent 26 and liner 28 could overlap to a lesser or greater extent than that shown in the Figures, and the stent may or may not extend through the target vessel wall.

For example, the stent 26 could extend along substantially the entire length of the conduit 18, along only the two end portions of the conduit, or the conduit could include discrete sections that comprise only stent or liner material. In the exemplary embodiment shown in FIGS. 1–4, the conduit 18 has a distal section defined by stent and liner material while the remaining length of the conduit 18 is defined by liner material alone (as seen from FIGS. 3A–3B). Also, while the stent 26 is shown disposed outside the liner 28 in FIGS. 1–4, it will be recognized that the stent may be disposed within the liner. Finally, while the illustrated conduit 18 includes only the stent 26 and a single liner 28, an additional layer(s) of material, such as another layer of PTFE or ePTFE, a layer of silicone, or another stent, may be included as well.

Referring to FIG. 2, the conduit 18 is supported by the shaft assembly 14, and more particularly by a support member 30 which forms part of the shaft assembly 14. The support member 30 may be a rod or shaft that is sized and configured to mount the conduit 18, and more specifically the stent 26 and liner 28. FIG. 2 shows (in phantom) the conduit 18 mounted on the support member 30 in its collapsed orientation. The support member 30 has a proximal end 32 and a distal end 34, the proximal end 32 being fixed to the handle 12 (as shown in FIGS. 3–4). The distal end 34 is preferably provided with a stop for maintaining the conduit 18 in position. The stop may be in the form of a piston 36 carried by the support member 30 and sized to generally correspond to the collapsed diameter of the conduit 18. The illustrated support member 30 also includes a bore 38 extending through the length of the member (FIG. 2).

In the illustrated embodiment, the bore 38 in the support member 30 receives a shaft 40 provided with a retention mechanism for retaining all or a portion of the conduit 18 (and in particular the stent 26) in its collapsed orientation during introduction into the lumen of the target vessel. A preferred retention mechanism comprises a sheath 42 sized and configured to be placed over a collapsed portion of the conduit 18. A nose cone dilator having one or more tapered surfaces for introducing the device into the lumen of a target vessel is preferably disposed on the shaft 40 distal to the sheath 42. The nose cone dilator may comprise any suitable material, a soft, floppy atraumatic material being preferred. It should be noted that alternative or additional means for dilating the vessel may be used or the dilator may be omitted altogether, although some form of dilator is preferably used. The sheath 42 is preferably fixed to the shaft 40 but could instead be removably supported by the shaft. The sheath 42 may be formed of any suitable thin-walled, flexible material, e.g., polyolefin, nylon, polyimide, PEEK, or Hytrel.

It will be appreciated that the sheath could be constructed so as to be removable in a manner the same as or similar to that disclosed in co-pending, commonly-owned application Ser. No. 09/232,103, filed on Jan. 15, 1999 and entitled "Methods and Devices for Forming Vascular Anastomoses," or co-pending, commonly-owned application Ser. No. 09/232,062, filed on Jan. 15, 1999 and entitled "Methods and Devices For Bypassing an Obstructed Target Vessel by Placing the Vessel in Communication with a Heart Chamber Containing Blood," the subject matter of which applications has been incorporated herein by reference.

Additionally, the sheath could be constructed according to the disclosure in co-pending, commonly-application Ser. No. 09/304,141, filed on May 3, 1999 and entitled "Methods and Devices for Forming a Conduit Between a Target Vessel and a Blood Source," the entire subject matter of which application is incorporated herein by reference.

As shown in FIG. 2, the proximal portion of the shaft 40 is in the form of a rack 44 which forms part of the actuator assembly 16. The actuator assembly 16 is used to impart relative movement to the conduit 18 and sheath 42 in order to deploy the conduit 18 in the target vessel. The rack 44 has teeth for engaging the teeth of a pinion 46 carried by an actuator 48. In the illustrated embodiment, the actuator 48 is a lever pivotally coupled to the handle 12 by a pivot pin 50. The actuator 48 is pivoted with respect to the handle 12 and transmits motion to the shaft 40 via the mating gear teeth on the rack 44 and pinion 46. The actuator assembly 16 is constructed so that pivoting the actuator 48 moves the shaft 40 and sheath 42 a desired amount in a desired direction to deploy the conduit, which according to the preferred embodiment may be done using one hand, as described more fully below. Other methods of actuation may of course be used, such as those using cable systems, alternative lever assemblies, etc. The device 10 also preferably includes a locking mechanism which may be in the form of a safety pin 52 movably disposed in a bore 54 in the handle 12. The safety pin 52 can be moved into or out of a mating bore 56 formed in the actuator 48 to either lock or unlock the actuator 48 with respect to the handle 12.

The device 10 also includes a mechanism that aids in removing the device, and in particular the sheath 42, from the target vessel. A preferred mechanism is indicated generally by the reference numeral 58 in FIG. 2 and comprises a tubular body 60 having a bore 62 sized to be slid over the support member 30. The body 60 has a proximal end 64 and a distal end 66, the latter being provided with a member 68 that is configured to be coupled to the sheath 42. The member 68 preferably has a tapered contour that allows the member 68 to be slid into the open end of the sheath 42. The member 68 may have a groove 70 or other portion that engages the edge of the sheath 42 to provide a smooth outer profile for withdrawing the sheath from the lumen of the target vessel.

The proximal end 64 of the tubular body 62 is provided with an actuating portion 72 for moving the body 62 and member 68 with respect to the shaft 40. The actuating portion 72 may be connected to the tubular body 62 by a stem 74 which extends through a slot 76 formed in the handle 12. The body 62 may be movable in one or more directions; in the illustrated embodiment, the tubular body 62 is moved distally (to the left in FIG. 3) along the longitudinal axis of the device to engage the member 68 and the sheath 42. The entire device is then moved proximally with the sheath 42 passing through the conduit 18.

As can be seen from FIG. 1, the relative position of the actuator 48 of assembly 16 and the actuating portion 72 of sheath removal mechanism 58 allows them to be operated using one hand. Accordingly, a surgeon may place the conduit 18 in fluid communication with the target vessel, remove the sheath 42 (or other retention mechanism) from the conduit, and remove the device 10 from the vessel using only one hand. This aspect of the invention provides the user with a free hand unlike an instrument requiring two-handed operation, and thus adds flexibility to enable relatively quick and easy conduit deployment. It will be recognized that the invention encompasses other device configurations that allow the conduit to be deployed and/or the device to be removed by one-handed operation, the particular device shown in the Figures being merely exemplary.

FIGS. 3–4 show in more detail the internal construction of the illustrated device 10. FIG. 3 shows the handle 12 and actuator assembly 16, while FIGS. 3A, 3B and 4 show details of the shaft assembly 14. The handle 12 preferably includes a chamber 80 that receives the rack 44 and pinion 46 of actuator assembly 16 and allows them to move upon actuation of the device. The rack 44 or pinion 46 may be constrained by a track or guide so as to move along a certain path or they may simply be disposed in the chamber 80 in a free-floating manner.

It should be noted that the device 10 may be introduced into a target vessel in various ways. For example, in the illustrated embodiment, the handle 12 of the device 10 is provided with a bore 82 that may receive an incising element (not shown) having a sharpened tip for penetrating the wall of the target vessel. See FIG. 3. The bore 82 opens into the chamber 80 and is aligned with a bore 84 provided in the shaft 40 (or another component of the shaft assembly 14). The incising element could be a separate component that is passed through the bores 82, 84; alternatively, the incising element could be formed as an integral part of the device. The invention could be used with other incising elements or components, for instance, the incising assembly disclosed in application Ser. No. 09/232,103 and application Ser. No. 09/232,062, the entire subject matter of which applications has been incorporated by reference herein.

Providing the shaft assembly 14 of the device with the bore 84 allows the incising element to be extended and retracted and also protects the conduit 18 by limiting or preventing its contact with other components of the device.

Additionally, either or both of the bores 82, 84 may be configured to act as a flashback lumen that indicates when the device has entered a lumen containing blood, for example, a coronary artery or heart chamber. The bores 82, 84 may be disposed to provide blood flash irrespective of whether the bores receive an incising element or an additional member(s), for example, means for introducing the device into the target vessel such as a guide wire or guide catheter. In addition, it will be appreciated that the device may be used without an incising element, for example, by placing the shaft assembly through a surgical incision in the target vessel wall.

Turning again to FIGS. 3–4, the device 10 is depicted in a first position (also shown in FIG. 1) wherein the conduit 18 has not yet been deployed in a target vessel. In this position the sheath 42 overlies a selected portion of the conduit 18 and holds the stent 26 and liner 28 in a collapsed orientation. The remaining portions of the stent 26 and the liner 28 extend outside of the sheath 42 and assume their expanded orientation. As seen in FIG. 3A, the sheath 42 contacts the outer surface of the portion of the stent 26 to maintain that portion collapsed. In the illustrated embodiment, the liner 28 is disposed within stent 26, although, as noted above this is only one possible construction. Also, the portion of the liner 28 within the sheath 42 is preferably folded or otherwise collapsed to a lower profile (although for sake of clarity FIG. 3A does not show the liner 28 folded to such a profile).

The shaft 40 extends through the bore 82 in the handle 12 and is disposed, preferably coaxially, within the bore 38 in the support member 30. The conduit 18 is loaded on the support member 30 and the desired portion of the conduit is collapsed to a low profile orientation, the piston 36 abutting the distal end 22 of the conduit 18. The sheath 42 is placed over the collapsed portion of the conduit 18 as shown in FIG. 1. The actuator 48 is moved toward the handle 12 which rotates the pinion 46 and drives the rack 44 distally (to the left in FIGS. 3–4). This moves the sheath 42 to uncover the stent 26 and deploy the conduit 18. Moving the sheath 42 in this direction will tend to move the conduit 18 in the same direction due to friction between the stent 26 and the sheath 42. The piston 36, however, prevents the stent 26 from moving with the sheath 42 (as the piston is fixed to the handle 12). As a result, the sheath 42 is moved while the conduit 18, including the stent 26, remains substantially stationary (and preferably stationary) with respect to the handle 12.

In the illustrated embodiment the actuator 48 is pivoted toward the handle 12; however, the device could be constructed so that the actuator 48 is moved in a different manner or direction to deploy the conduit. For example, the actuator assembly 16 could comprise a trigger-like member that is slideable with respect to the handle 12, or a pair of scissors-like members that are moved together (or apart) to actuate the device. An actuator that is operable using one hand is preferred, although not necessary to practicing various aspects of the invention. At any rate, the actuator assembly 16 is preferably coupled to the shaft assembly 14 so as to produce motion that is generally along the longitudinal axis of the device, thereby providing the device with a small profile, although a non-longitudinal actuator motion could also be used.

Figure 5A:
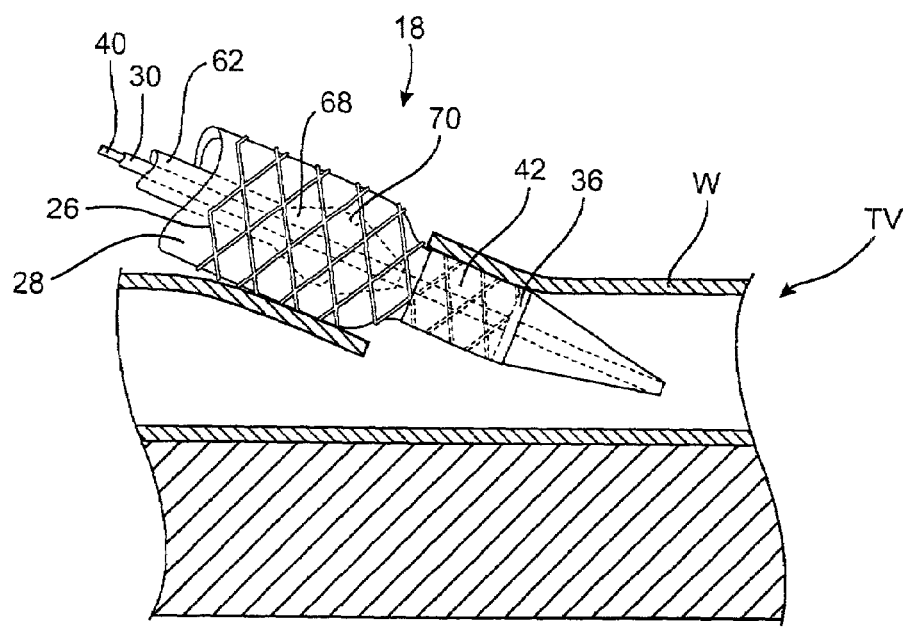
FIGS. 5A–5D are sectional views sequentially illustrating an exemplary use of the device shown in FIG. 3.

FIGS. 5A–5D illustrate an exemplary application of the device 10 wherein a conduit is placed in fluid communication with a target vessel TV. FIG. 5A shows the distal portion of the shaft assembly 14 inserted through an opening in the target vessel wall W and into the lumen of the target vessel.

Although not shown, an incising component may be used to form the opening in the wall W. The device 10 is preferably introduced into the lumen by dilating the opening in the wall W and cannulating the target vessel TV.

Figure 5B:
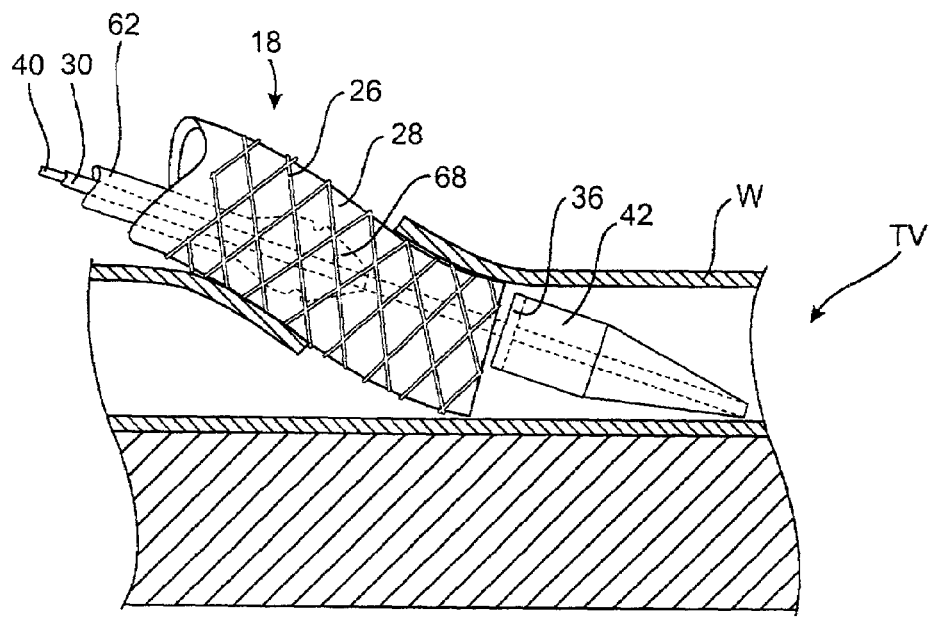

FIG. 5B shows the device after the sheath 42 has been moved distally to expose the portion of the conduit 18 that is covered by the sheath in FIG. 5A. The actuator 48 is moved relative to the handle 12 from the position shown in FIG. 1 to move the sheath 42 and allow the stent 26 to assume its expanded orientation. The piston 36 prevents the stent 26 from moving distally with the sheath 42. This step is preferably carried out so as to prevent or minimize trauma to the target vessel TV, so the nose cone dilator is formed of a relatively soft and flexible material and has an atraumatic shape, although stiff or rigid materials may be used as well. In the position shown in FIG. 5B, the stent 26 is fully expanded and secures the deployed conduit 18 to the target vessel TV in fluid communication therewith, preferably via a sealed connection between the two structures.

As can be seen from FIG. 5B, the piston 36 is disposed in (or near) the proximal end of the sheath 42 after the stent 26 has been deployed in the target vessel TV. As such, the piston 36 may block the open end of the sheath 42 and interfere with engagement between the sheath removal mechanism 58 and the sheath 42. Accordingly, it may be necessary to first impart relative movement to the piston 36 and the sheath 42 in order to present an open proximal end of the sheath to the removal mechanism 58. This may be achieved in various ways. For example, in the illustrated embodiment the piston 36 is fixed to the handle 12 via support member 30. The actuator 48 thus may be moved away from the handle 12 to move the sheath 42 proximally with respect to the handle and the piston 36. Alternatively, the piston 36 could be coupled to the handle so as to be movable with respect thereto, e.g., by a separate actuator. In either case the piston 36 is moved relative to the sheath 42, an exemplary result of such movement being shown in FIG. 5C.

It will be recognized that other constructions may of course be used. For example, rather than imparting relative movement to the piston 36 and the sheath 42, the sheath removal mechanism 58 could be configured to engage the edge of the sheath 42 without moving the piston. Also, the mechanism 58 could be configured to engage the piston 36 directly and provide a smooth outer profile to the distal portion of the shaft assembly 14.

Figure 5C:
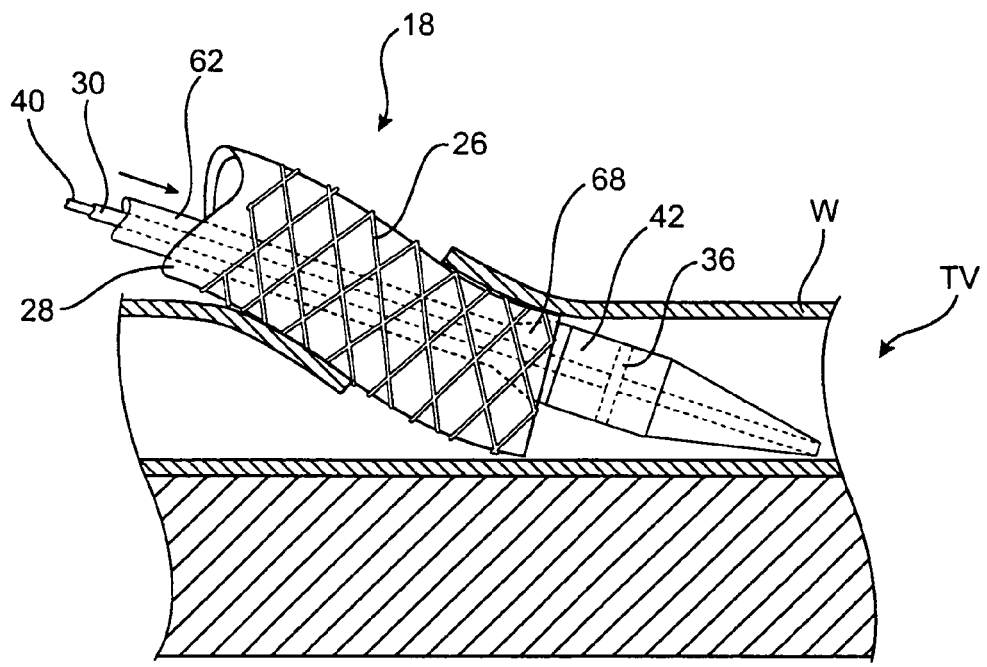
Figure 5D:
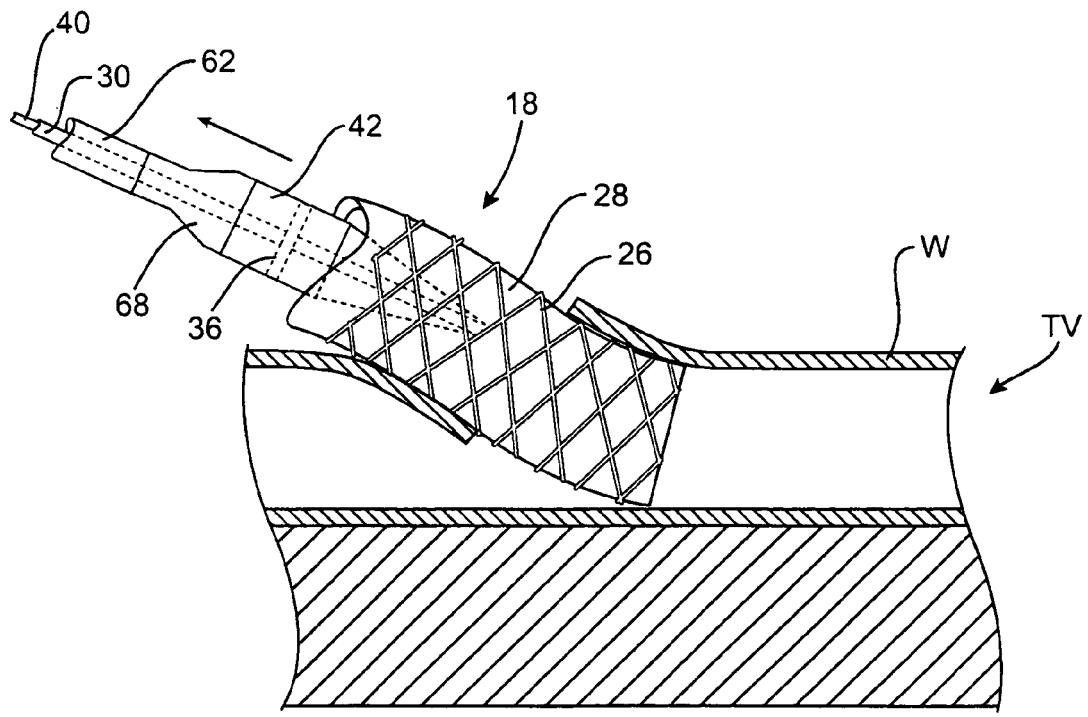

FIG. 5C shows the sheath removal mechanism 58 after it has been moved in the direction of the arrow into engagement with the open end of the sheath 42 to form a smooth atraumatic profile that prevents or minimizes damage to the vessel or the conduit 18. In the illustrated embodiment the edge of the sheath 42 rests in the groove 70 and transitions into the proximal portion of the member 68. The next step, as shown in FIG. 5D, is to move the shaft assembly 14 proximally in the direction of the arrow to remove the device and deploy the conduit 18 in the target vessel TV. The removal mechanism 58 prevents the sheath from catching on the stent struts. Removing the device results in a preferably fluid-tight attachment that communicates the lumen of the conduit 18 with the lumen of the target vessel TV.

Figure 6:
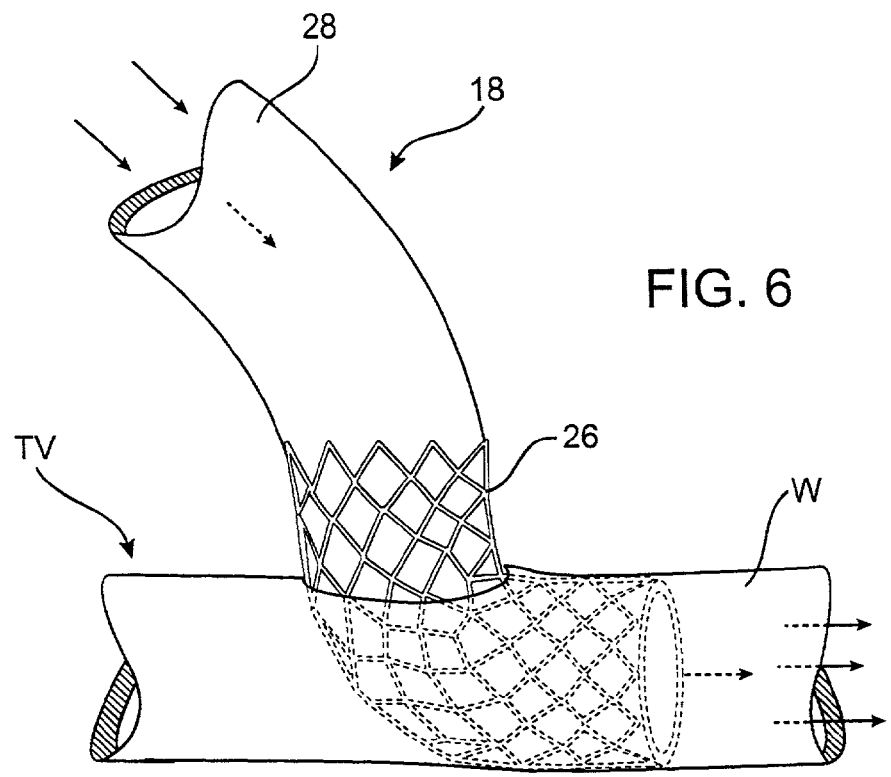
FIG. 6 is a perspective view of a conduit that has been placed in fluid communication with a target vessel as shown in FIGS. 5A–5D, the conduit including a vessel coupling disposed on the exterior of the conduit.

FIG. 6 is a perspective view of the exterior of the target vessel TV and the conduit 18. The distal end 22 of the conduit 18 is positioned in the lumen of the target vessel TV with the stent 26 expanded against the vessel wall W. The liner 28 is secured to the stent 26 and thus is held open by the expanded stent to provide a fluid path for blood flowing in the direction of the arrows. The amount of the conduit 18 that is positioned in the lumen of the target vessel TV may vary from that shown but is preferably sufficient to ensure a secure attachment between the conduit and the vessel. Similarly, the amount of the stent 26 that extends outside the target vessel TV may vary from that shown in FIG. 6. However, as noted above it may be desirable to allow a sufficient portion of the stent 26 to extend through the opening in the target vessel wall to prevent the vessel wall from collapsing the conduit 18.

Figure 6A:
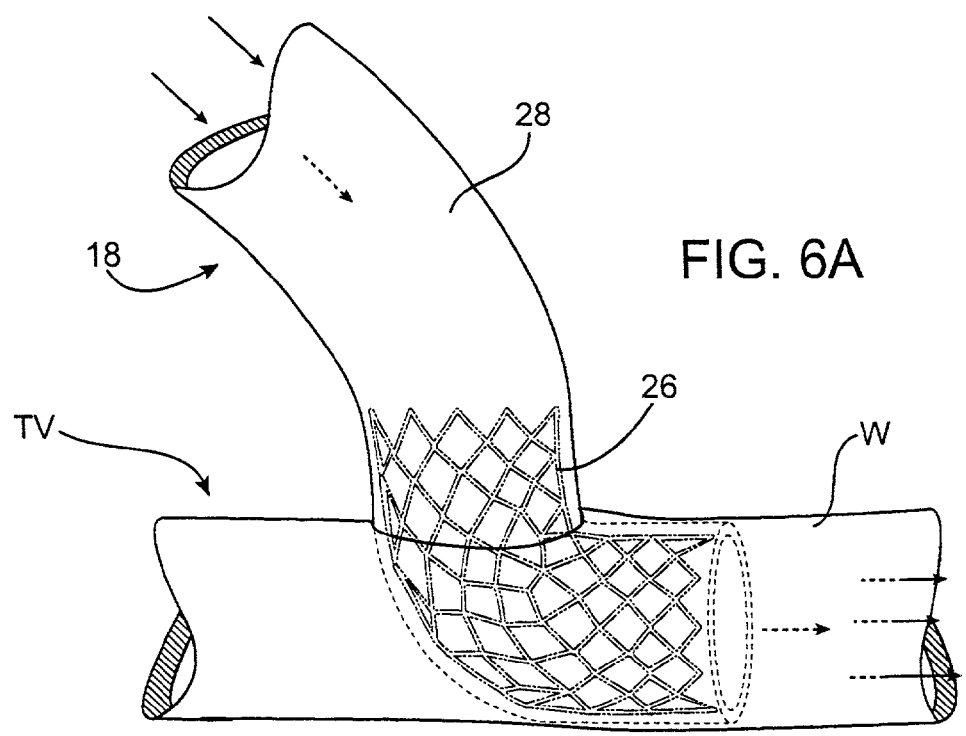
FIG. 6A is a perspective view of the conduit shown in FIG. 6, wherein the vessel coupling is shown disposed within the conduit.

FIG. 6A shows an alternative embodiment wherein the stent 26 is disposed on the interior of the conduit 18, and specifically within the interior of the liner 28. In this arrangement the liner 28 is forced open by the expanded stent to provide an open fluid path for blood flowing in the direction of the arrows. It should be noted that in this embodiment the liner 28 may be secured to the stent 26 less vigorously as the stent presses the liner against the target vessel wall, as opposed to the stent pulling the liner toward the wall (as in the embodiment of FIG. 6). It will be appreciated that other constructions and configurations may be used as well.

Figure 7:
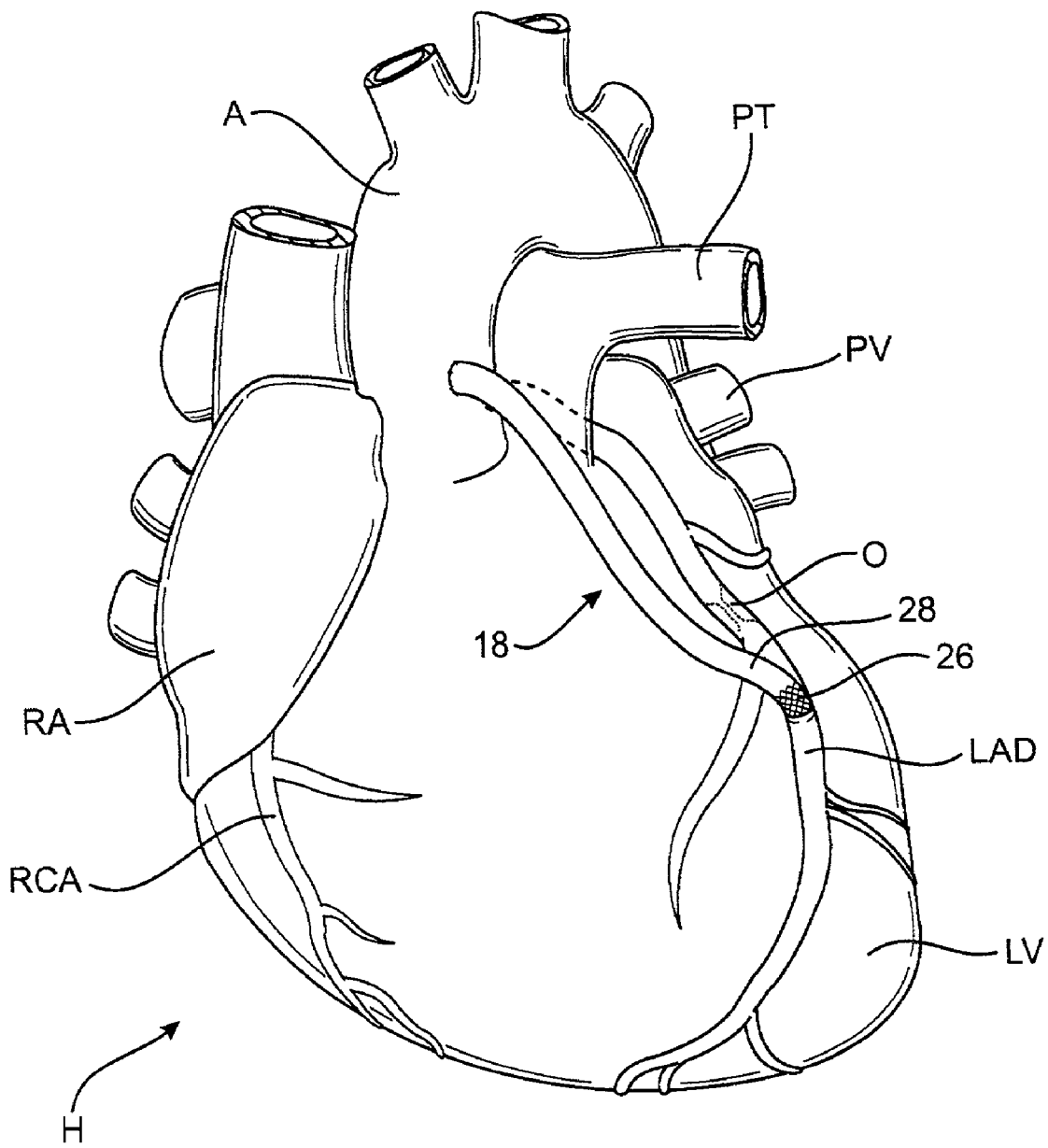
FIG. 7 is a perspective view of a conduit that has been placed in fluid communication with a target vessel and a source of blood according to another embodiment of the invention, wherein the source of blood is the aorta.

FIG. 7 is an anterior view of a heart H showing the left ventricle LV, right atrium RA, aorta A, pulmonary trunk PT and pulmonary veins PV. The left coronary artery, including the circumflex branch and the left anterior descending branch LAD, is visible in this view, as is the right coronary artery RCA. The coronary arteries run along the heart wall and deliver oxygenated blood to the myocardial tissue. An occlusion or blockage O partially (or completely) obstructs the lumen of the LAD, which results in inadequate or no blood flow to the heart wall tissue fed by the portion of the LAD that is downstream of the occlusion O.

The distal end 22 of the conduit 18 has one end secured to the LAD (distal to the occlusion O) by the stent 26 as described above. The proximal end 20 of the conduit 18 is secured to a source of blood, which in this case is the aorta A. The proximal end 20 may be attached to the aorta A via a sutured anastomosis P created by an instrument or in a hand-sewn manner. Other means for attaching the end of the conduit 18 include a vessel coupling such as a stent, other fasteners, biologically compatible adhesives, etc. Also, as an example, the length of the conduit extending between the aorta and the coronary vessel may be in the range of from about 5 cm to about 8 cm (including the portion of the conduit disposed in the vessel).

Figure 8:
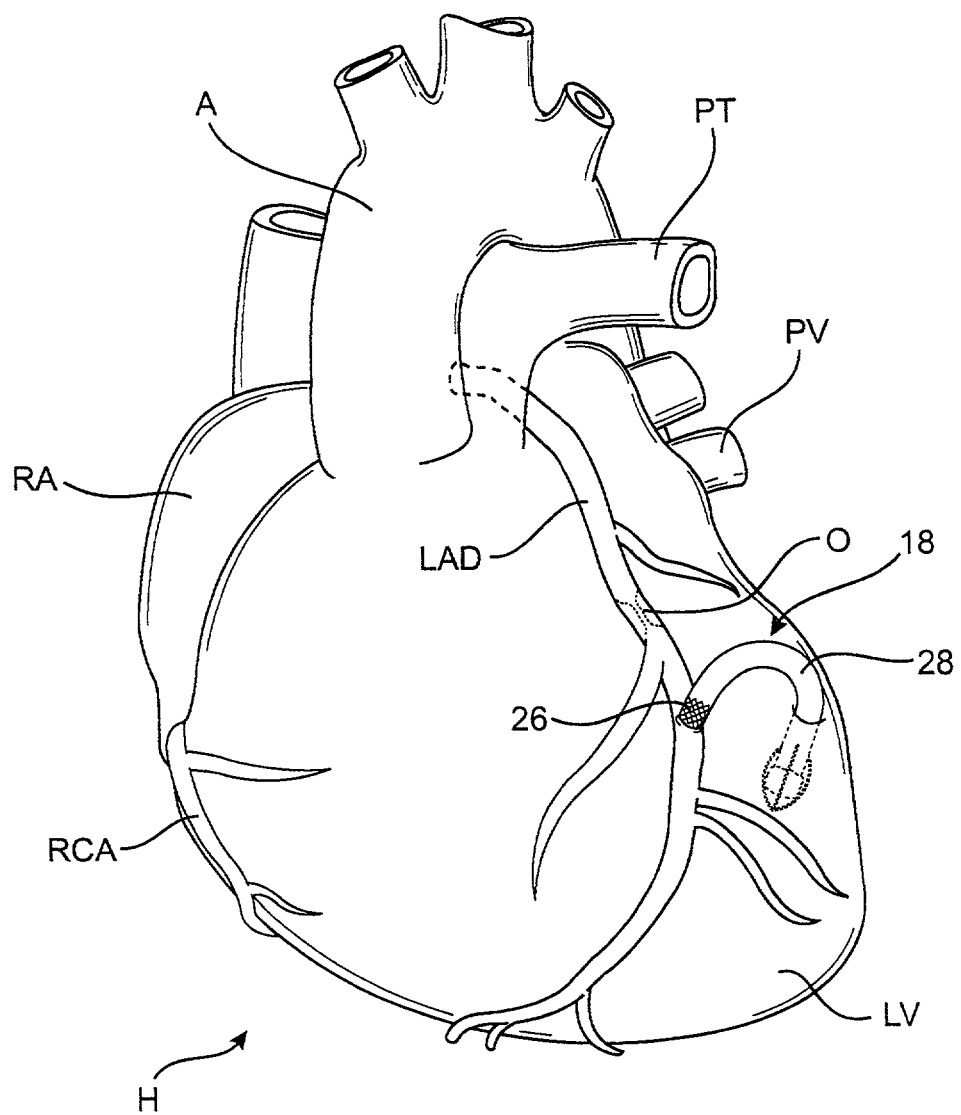
FIG. 8 is a perspective view of a conduit that has been placed in fluid communication with a target vessel and a source of blood according to another embodiment of the invention, wherein the source of blood is the left ventricle and the conduit has an end configured to be placed in the myocardium.

It will be appreciated that the particular target vessel and source of blood shown in FIG. 7 is only exemplary as there will be numerous applications for the methods and devices disclosed herein. For example, FIG. 8 illustrates a heart wherein the invention has been used to place a target vessel in fluid communication with an alternative source of blood. The distal end 22 of the conduit 18 is secured to the LAD as in FIG. 7; however, the proximal end 20 of the conduit is placed in fluid communication with a heart chamber containing blood, which in this embodiment is the left ventricle LV. As a result, blood flows from the left ventricle LV into the conduit 18 and into the target vessel distal to the occlusion O. As an example of one possible configuration, the length of the conduit extending between the heart chamber and the coronary vessel may be in the range of from about 3.5 cm to about 5 cm (including the portion of the conduit disposed in the myocardium).

Figure 10:
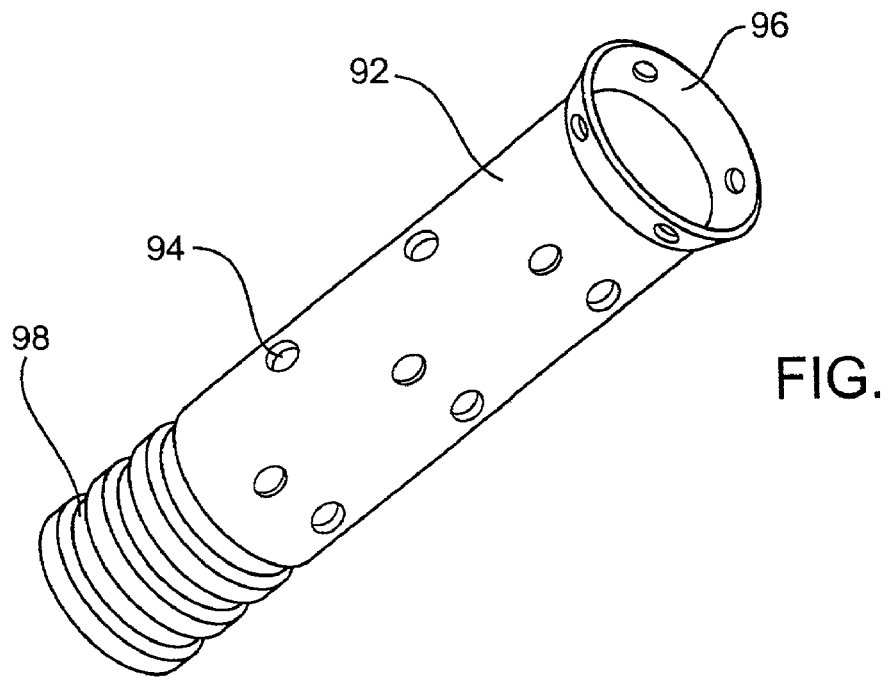
FIG. 10 is a perspective view of a fitting mounted to the end of the conduit shown in FIG. 9.
Figure 9:
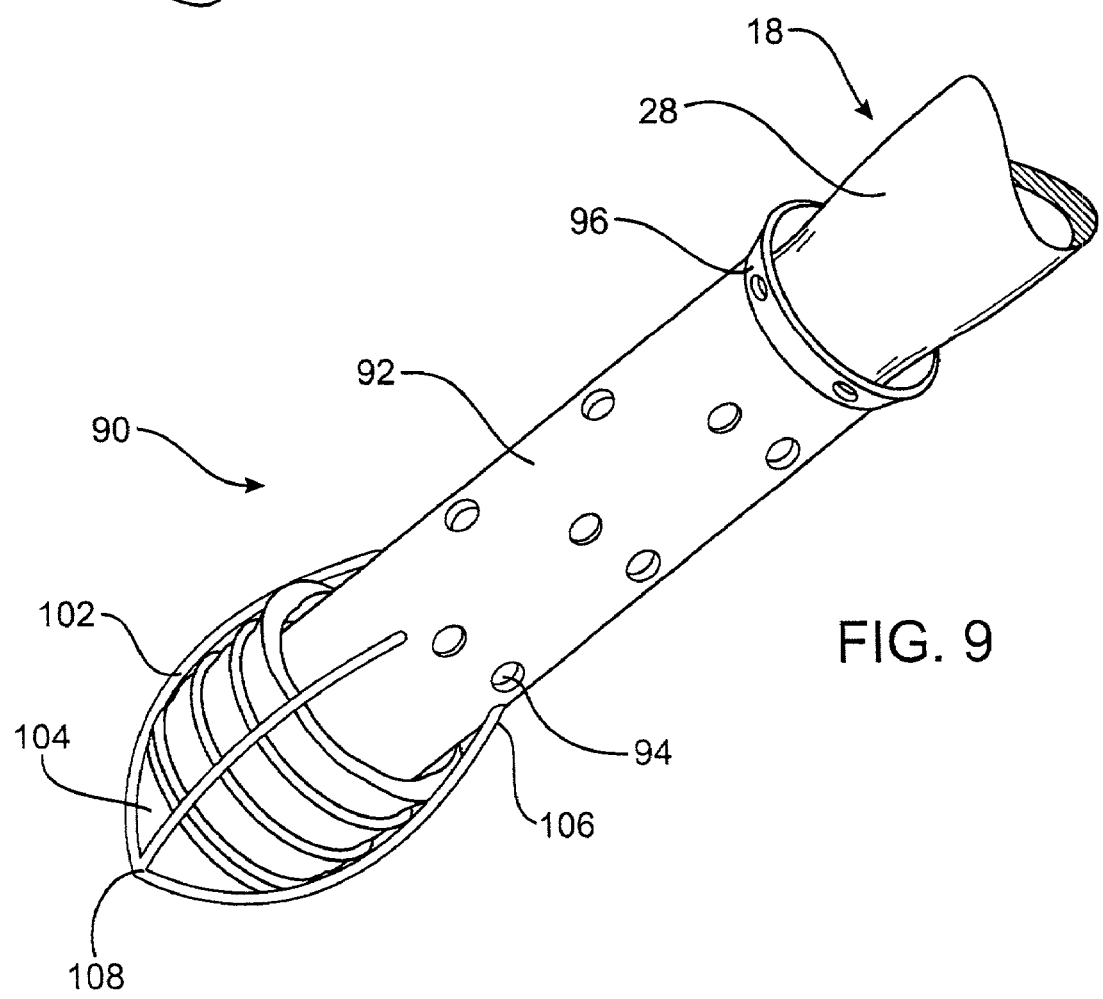
FIG. 9 is an enlarged perspective view of an end of the conduit that is shown placed in the left ventricle in FIG. 8.

FIG. 8 also illustrates a device for securing an end of the conduit to tissue located adjacent the source of blood. The device is indicated generally by the reference numeral 90 and is shown in detail in FIGS. 9–11. FIG. 9 is an enlarged view of the distal end 22 of the conduit 18 coupled to the device 90 as shown in FIG. 8. FIG. 10 is an enlarged view of a fitting 92 which forms part of the device 90. FIG. 11 is an enlarged view of a tissue section T showing one preferred placement of the device 90 so as to communicate with a source of blood S.

The fitting 92 preferably comprises a tubular member with opposite ends opening into a hollow interior. The fitting 92 may be formed of any suitable material having sufficient strength to remain open against compressive forces exerted by the tissue. Suitable materials include stainless steel, titanium, tantalum, polymers, etc. The dimensions of the fitting 92 may be varied depending on the particular application and the material(s) used. As an example, for use in the application illustrated in FIG. 8, the fitting 92 may be formed from 6 or 8-gauge thin wall 304 stainless steel hypo tube stock with a length of approximately 23 mm and an OD of approximately 5 mm.

The fitting 92 may be provided with one or more openings 94 for securing the liner 28 to the fitting or better fixing the position of the fitting in tissue. The fitting 92 also may be provided with a flange 96 at an end thereof for engaging tissue and further securing the device 90 in position. As shown in FIG. 10, another end of the fitting 92 is provided with one or more grooves 98 for use in securing the conduit 18 to the fitting. FIG. 9 illustrates the conduit 18 passed through the interior of the fitting 92 with the distal end 22 of the conduit everted over the end of the fitting. In the illustrated embodiment, one or more lengths of suture extend around the everted distal end 22 of the conduit 18 and lie in the grooves 98 so as to secure the conduit to the fitting 92. It will be appreciated that the lengths of suture may be omitted or replaced by alternative fastening means, for example, biologically compatible adhesives, clips, bands, wire, etc.

The preferred embodiment of the conduit also includes a component for preventing blockage of the end of the device that is placed in communication with the source of blood. The component includes sufficient structure to prevent blockage and at least one opening through which blood from the source may enter the conduit. As an example, when placing a conduit in communication with a heart chamber, such as the left ventricle, an end of the conduit is positioned in and extends through the myocardium. The conduit end will move relative to the myocardial tissue, and particularly the endocardium, which may result in tissue overlying all or a portion of the open end of the conduit. The end of the conduit that is in the ventricle will also be located near tissue such as the chordae tendineae, papillary muscle or other myocardial tissue, thereby increasing the risk of such tissue blocking blood flow into the conduit.

One preferred component for preventing blockage of the conduit is indicated by the reference numeral 100 in FIGS. 9 and 11 and is provided on the device 90. The component 100 is in the form of a structure comprising a plurality of struts 102 defining open areas 104 through which blood may flow. Each strut 102 has one end 106 secured to the fitting 92 while the other ends of the struts meet at a junction 108. The struts 102 may be formed of various materials, for example, stainless steel wire or any of the materials used to form the fitting, and the ends 106 may be secured to the fitting 92 by any suitable means, e.g., brazing, welding, adhesives, etc. As an example, the struts 124 may be formed from 304 full hard stainless steel wire with a length of approximately 18 mm and an outer diameter of approximately 0.375 mm. If constructed as in the illustrated embodiment, the length of the portion of each strut 124 extending beyond the proximal end 120 of the vessel 112 may be approximately 8 mm.

While the illustrated mechanism includes three curved struts 104, fewer or more struts may be used, and the struts may be straight, curved, or otherwise shaped, and may be rigid or flexible. Further, it will be readily appreciated that alternative mechanisms for preventing blockage of the end of the conduit that communicates with the heart chamber (or other blood source) may be used in lieu of that illustrated in the Figures. For example, rather than a plurality of individual struts, the mechanism could comprise a grid or mesh that allows blood to flow into the conduit.

FIG. 11 schematically illustrates one possible orientation of the device 90 in tissue wherein the flange 96 engages an exterior surface of the tissue and aids in fixing the device in position. The openings 94 may be provided in order to enhance fixation of the device 90 in the tissue. For example, the openings 94 in the flange 96 may receive suture (not shown) that secures the fitting to tissue. In addition, the openings 94 in the flange 96 may be filled with a penetrable material, such as silicone, for holding various devices or instruments, e.g., needles, forceps, etc. For instance, a surgeon may use the material as a needle holder while performing a suturing procedure.

The component 100 is positioned so as to be partially disposed within the tissue T with a portion extending into the blood source S. The distal end 22 of the conduit 18 is positioned so as to extend slightly into the blood source S. The portion of the component 100 disposed in the blood source S acts as a barrier while allowing blood to enter the conduit 18. For instance, the end of the conduit that is placed in the ventricle will be located near tissue such as the chordae tendineae, papillary muscle or myocardial tissue, thereby creating a risk of such tissue blocking the flow of blood into the conduit. The struts 102 located in the blood source S will prevent (or minimize) obstruction of the distal end of the conduit 18 by such tissue, it being appreciated that the length of the struts and the extent to which they extend into the blood source may vary from that shown. In addition, the component 100 will prevent or minimize tissue being forced into the fitting 92 during placement of the fitting in the myocardium.

The embodiment of FIGS. 9–11 may rely on blood flow through the conduit 18 to maintain the liner 28 fully (or substantially fully) open within the interior of the fitting 92. However, it may be desirable in some instances to positively secure the liner 28 to the fitting 92 so as to ensure that the conduit 18 remains open under varying conditions, e.g., pressure differences occurring during the systolic and diastolic phases of the heart cycle. FIGS. 12 and 12A illustrate one embodiment in which the liner 28 is positively secured to the fitting 92, the means for securing the liner 28 comprising a layer 110 of silicone disposed along all or a portion of the device 90.

The layer 100 of silicone fills the space between the exterior of the liner 28 and the interior of the fitting 92, the silicone acting as a biologically compatible adhesive that maintains the liner against the wall of the fitting. The silicone flows into the openings 94 in the fitting 92 which enhances attachment of the liner 28. In the illustrated embodiment the openings 94 have a flared end 112 opposite the liner 28. The ends 112 receive the silicone so that each opening 94 forms a rivet-like plug of silicone that securely holds the liner 28 to the fitting 92. See FIG. 12A. Also, as shown in phantom in FIG. 12A, silicone (or another material) may be placed on the exterior of the rivet-like plug to provide a more secure connection.

In addition, the device 90 preferably includes another layer 114 of silicone disposed over the proximal end of the fitting 92 as well as over a portion of the struts 102 of the component 100. The layer 114 may be used to provide a smooth coating that covers the edges of the struts 102 and the fitting 92 to avoid or minimize trauma to tissue.

The device 90 may also be provided with means for preventing the conduit 18 (and in particular the liner 28) from collapsing during use. One suitable means is a strain relief element 116 that surrounds the liner 28, as shown in FIG. 12. The strain relief element 116 may be a helical wire, such as stainless steel or nitinol, that is wrapped around the liner 28. The strain relief element may extend over all or a portion of the length of the conduit. If a layer of silicone is used as in the illustrated embodiment, the element 116 may be bonded to or embedded in the silicone.

Other means for preventing the liner 28 from collapsing include placing an internal support member in the liner, such as a stent (as shown in FIG. 6A), that maintains the conduit open. Alternatively, the conduit, e.g., the liner 28, may be constructed in a preformed shape that will resist kinking or collapsing; for example, the conduit may be coated with a material that provides a desired amount of rigidity, such as silicone, polyurethane, PTFE, or other polymers. The coating is preferably on the exterior of the liner 28 to maintain the ePTFE-blood interface. The liner 28 may be provided with additional coatings selected to provide particular qualities, such as heparin coatings. As another alternative, which may be used in addition to or in lieu of providing the conduit with a strain relief element to prevent kinking, the portion of the conduit extending through the myocardium, such as the fitting 92 in FIGS. 8–12, could be specifically formed to prevent kinking. For instance, the fitting 92 could be L-shaped with a bend to prevent kinking at the junction of the fitting and the remainder of the conduit, the conduit including straight or tapered walls. Other configurations may of course be used as well.

Figure 13:
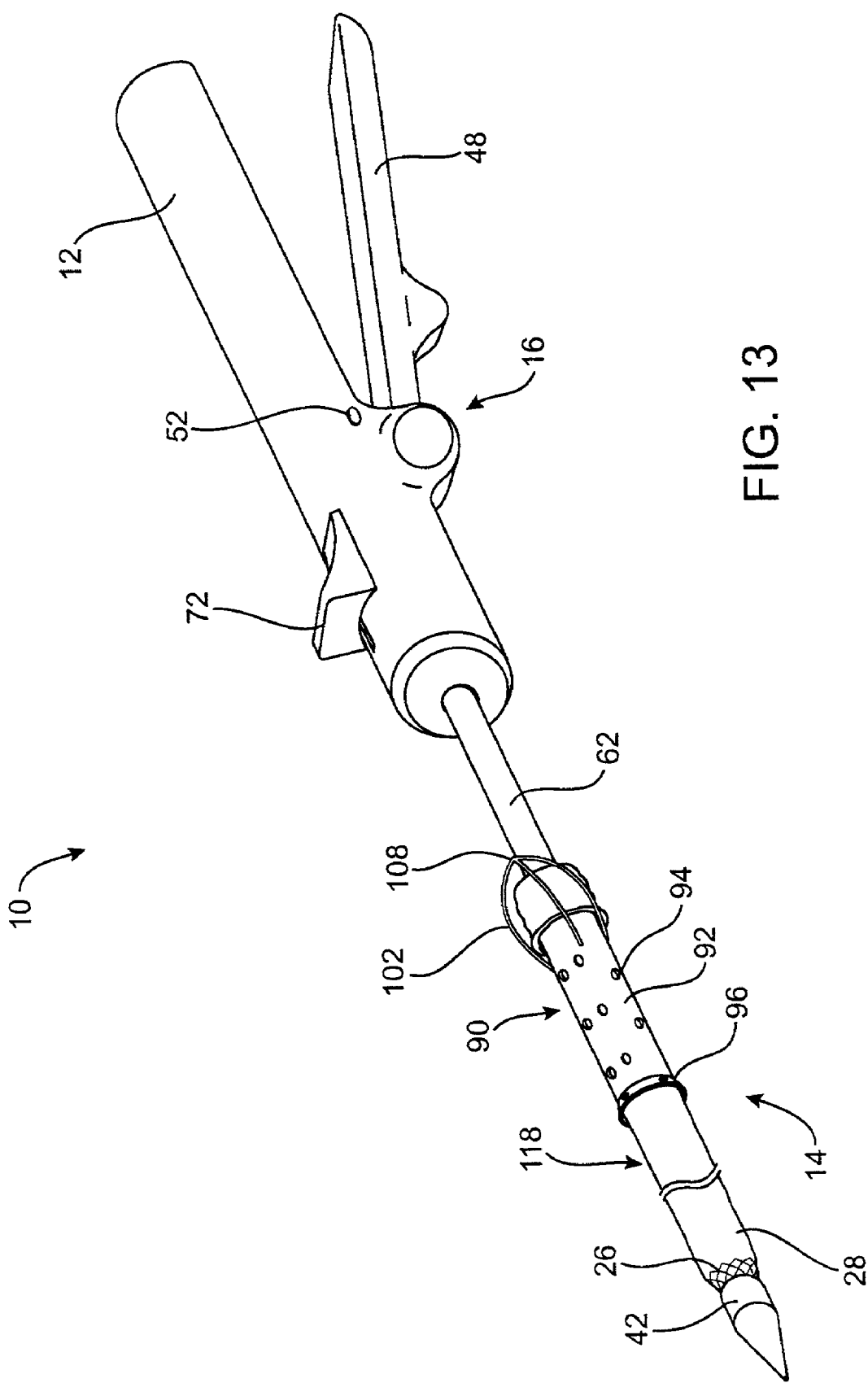
FIG. 13 is a perspective view of a device constructed according to another embodiment of the invention, wherein the device includes the conduit shown in FIG. 9.

FIG. 13 is a perspective view of another embodiment of the invention comprising a device (which may have the same construction as the device 10 shown in FIG. 1) provided with a conduit 118 specifically configured to be placed in communication with a heart chamber. The conduit 118 is loaded on the shaft assembly 14 and has a distal end constructed as described above and a proximal end provided with the device 90 shown in FIG. 9. The device 90 is adapted to be placed in fluid communication with a source of blood such as the left ventricle. The fitting 92 is placed in the tissue of the myocardium so that the component 100 and the distal end of the fitting 92 project slightly into the heart chamber, as shown in FIG. 11.

Figure 14:
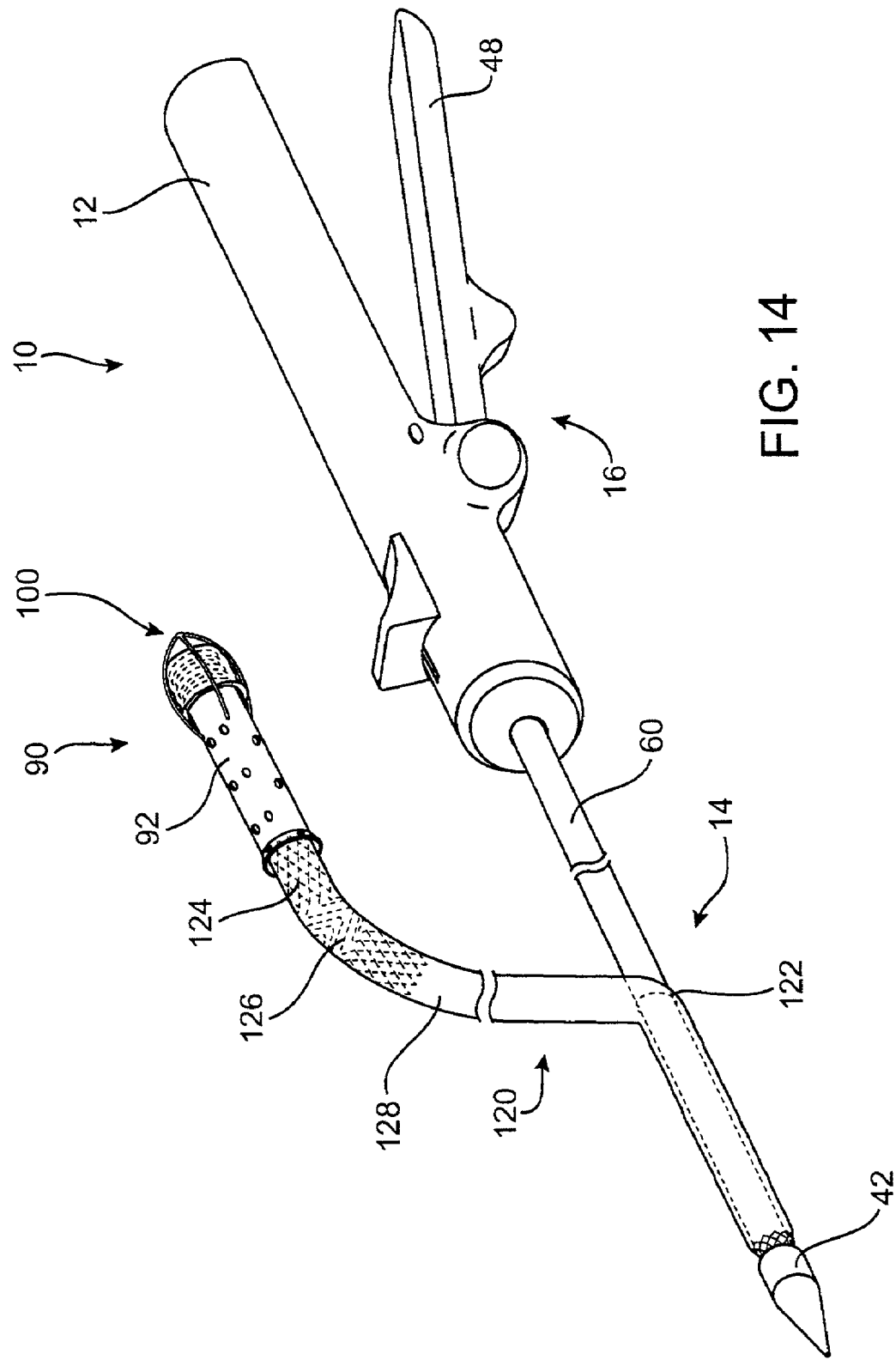
FIG. 14 is a perspective view of a device constructed according to another embodiment of the invention for placing a conduit in fluid communication with a target vessel and a source of blood, wherein the device allows placement of either end of the conduit first.

FIG. 14 is a perspective view of still another embodiment of the invention comprising a device (which also may have the same construction as the device 10 shown in FIG. 1) provided with a conduit 120. The conduit 120 is loaded on the shaft assembly 14 and preferably has a distal end constructed as in the previous embodiments. The conduit 120 also has a proximal end including a device 90 (and component 100) that is adapted to be placed in fluid communication with a heart chamber and is preferably constructed as in the previous embodiments. It should be understood, though, that this embodiment may be practiced with a conduit that is adapted to be placed in communication with another blood source, such as the aorta.

This embodiment of the invention allows a conduit to be placed in fluid communication first with a source of blood and then with a target vessel, or vice-versa. Placing the conduit in communication with the blood source first may be useful to de-air the conduit, i.e., force air from the conduit interior, prior to securing the conduit to the target vessel. FIG. 14 shows one construction wherein the conduit 120 has an opening 122 through which the a portion of the shaft assembly 14 passes. The proximal end of the conduit 120 including the device 90 may be positioned in the myocardial tissue, for example, through an incision made in the myocardium. The positive pressure in the heart chamber (especially the high pressures present in the left ventricle during systole) forces air through the conduit 120 and out the distal end adjacent the sheath 42. The opening 122 may be substantially sealed against the shaft assembly 14 of the device to force air toward the distal end of the conduit 120.

The embodiment exemplified in FIG. 14 permits either end of the conduit 120 to be placed first, which may be used to de-air the conduit as described above. This feature of the invention also provides flexibility so that in a given procedure the user has the option to first secure the conduit to either the blood source or the target vessel, which may be beneficial, for example, in a multi-vessel bypass procedure where access to different areas of the heart is obtained by temporarily moving or retracting all or a portion of the heart.

The opening 122 in the conduit 120 is preferably formed to allow its closure during the procedure. For instance, the conduit 120 could be clamped proximal to the opening 122 after the proximal end of the conduit has been placed in communication with the blood source and the conduit de-aired. The distal end of the conduit 120 could then be deployed in the target vessel and the shaft assembly removed through the opening 122. Air would be forced out of the conduit and the opening 122 then sealed by a patch formed of tissue or synthetic vascular graft material such as ePTFE. The patch (not shown) could by fixed to the conduit by various means, e.g., suture, clips, biologically compatible adhesives, etc. Alternatively, the conduit 120 could include a collapsible, foldable or crimpable member which is sealed closed after the shaft assembly 14 has been removed from the conduit. It will be recognized that an opening into the conduit could be formed at any location along the length of the conduit and in any component forming part of the conduit, for example, in the fitting 92 of device 90.

The illustrated conduit 120 also is provided with means for preventing the conduit from collapsing or kinking. The proximal end 122 of the conduit (or more of the conduit, if desired) is provided with an internal support 124 to maintain the lumen of the conduit 120 open. The support 124 may be in the form of a self-expanding stent formed of a suitable material such as nitinol, titanium or tantalum. The support 124 preferably includes an articulated portion 126 that supports a curved section of the conduit 120 (and in particular the liner 128). The conduit is preferably rigid enough to remain open while being somewhat flexible. The conduit may be preformed to assume a desired orientation that provides an optimum blood flow path or achieves particular flow characteristics. Also, while the support 124 is shown disposed within the conduit 120 it may instead surround the exterior of the conduit.

The device of the invention may be sized and configured differently from that specifically illustrated in the Figures. As an example of a range of possible constructions, the device may be relatively short with the shaft assembly substantially rigid for use in an open-chest procedure. The device may be configured for use in either a minimally invasive or endovascular procedure, wherein the actuators for controlling the device components are located adjacent the proximal end of the device to allow remote deployment of the conduit.

Figure 15:
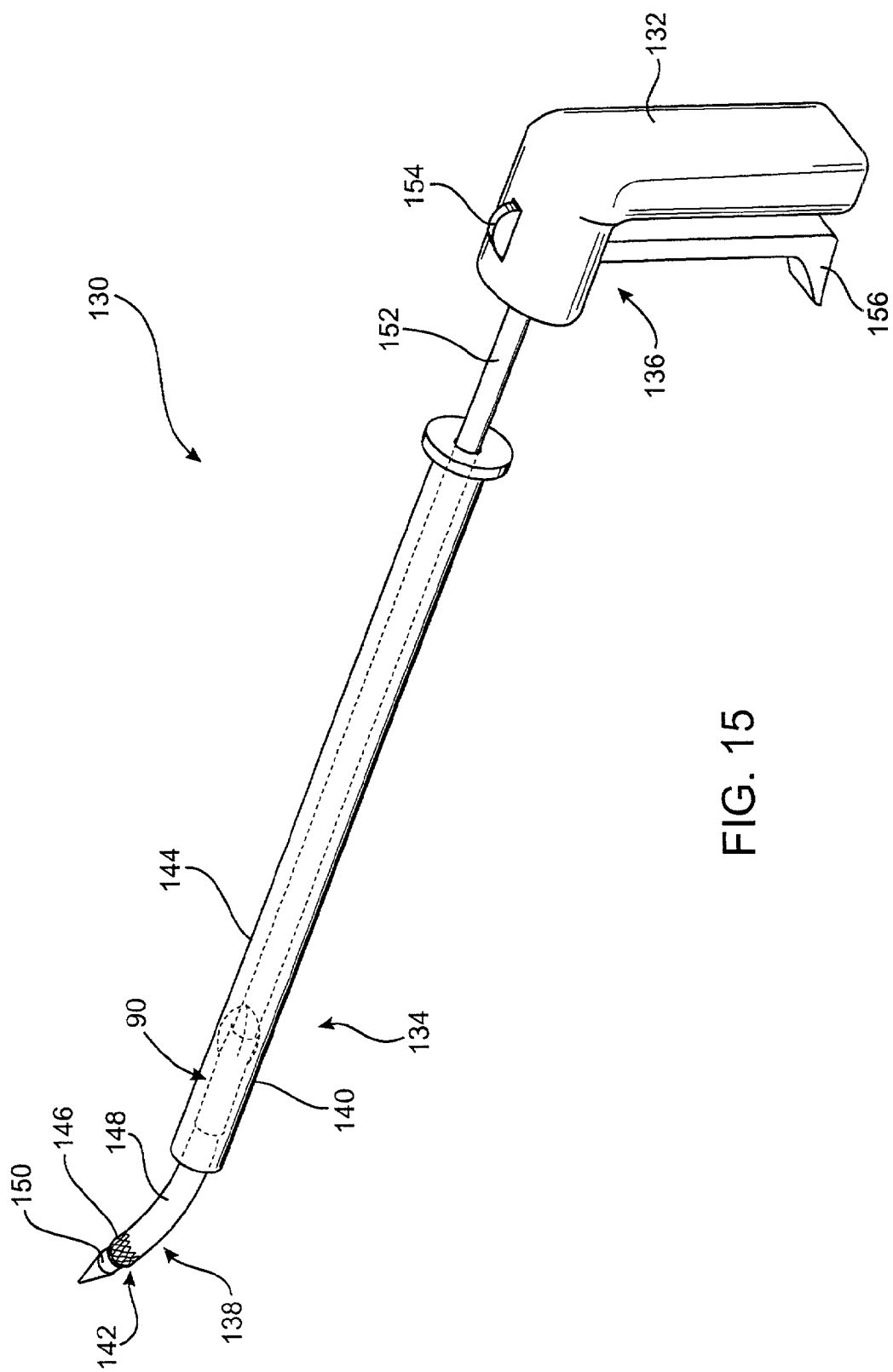
FIG. 15 is a perspective view of a device constructed according to yet another embodiment of the invention for placing a conduit in fluid communication with a target vessel, wherein the device is sized and configured for use in a laparoscopic or endoscopic procedure.
Figure 16:
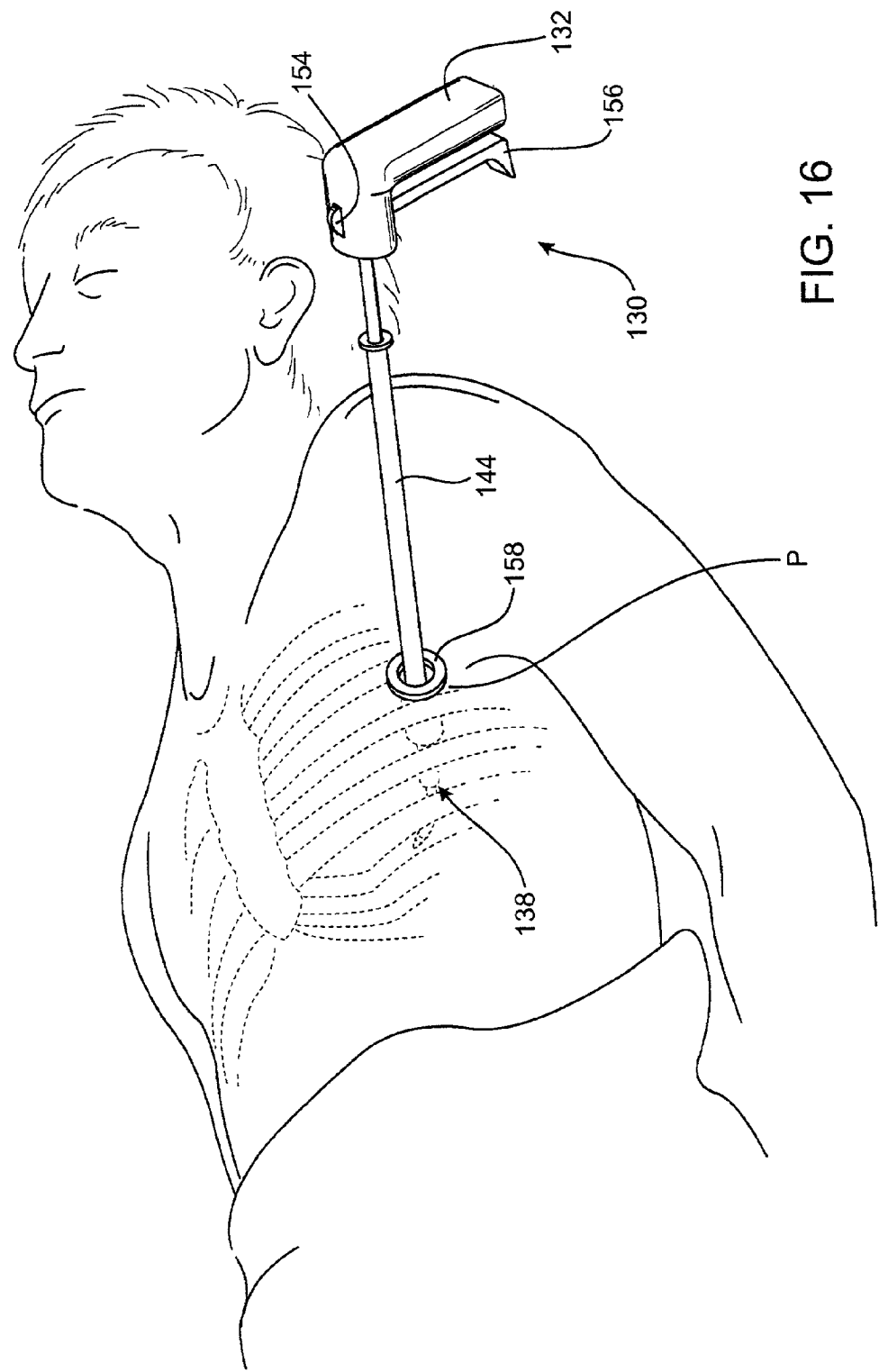
FIG. 16 is a perspective view illustrating the device shown in FIG. 15 being used in a minimally invasive procedure.

FIG. 15 is a perspective view of such a device constructed according to another embodiment of the invention. The device 130 is designed for use in a minimally invasive (e.g., laparoscopic, thoracoscopic or endoscopic) procedure. The device 130 has a similar construction to the device 10 described above and includes a handle 132, a shaft assembly 134 and an actuator assembly 136. The shaft assembly 134 supports a conduit 138 having a proximal end 140 and a distal end 142. A tubular access device 144 may be provided so as to be moveable over the shaft assembly 134 and is adapted to be passed through an opening in the patient's body. For example, the opening could be a thoracotomy passing through the chest wall for performing a thoracoscopic procedure (as shown in FIG. 16), or it could be laparotomy passing into the abdominal cavity to allow the chest cavity to be accessed through the diaphragm. The device 144 may have a flange or other portion to grip and manipulate the device with respect to the conduit 138 during use.

The conduit 138 is similar to the conduit 18 shown in FIG. 13 and comprises a vessel coupling in the form of a stent 146 coupled to a liner 148. A sheath 150 is disposed over the distal end 148 of the conduit 138 and holds the end in a collapsed orientation as explained above with respect to previous embodiments. The shaft assembly 134 preferably includes a sheath removal mechanism the body 152 of which is visible in FIG. 15. The actuator assembly 136 includes a first actuator 154 for controlling the sheath removal mechanism (which operates as described above), and a second actuator 156 for controlling the position of the sheath 150 with respect to the conduit 138. As in the previous embodiment, the actuators 154, 156 are preferably arranged to permit the conduit 138 to be deployed in the target vessel via a one-handed operation, with the actuator 156 moving the sheath 150 to deploy the conduit and the actuator 154 removing the sheath 150 from the conduit 138.

FIG. 16 shows schematically one possible application for the device 130 wherein a port P has been formed between a patient's ribs to access the chest cavity and the heart (not shown). A trocar sleeve or like structure 158 may be used to form the port P and one or more retractors (not shown) may be used as well. The device 130 is shown positioned through the trocar sleeve 158 with a distal portion of the shaft assembly 134 including the conduit 138 extending into the chest cavity. The actuator assembly is preferably located at or near the proximal end of the device 130 which allows easy actuation to deploy the conduit 138 in the target vessel. Additional ports P may be provided to introduce additional instruments into the chest cavity. For example, the device 130 could be used to deploy the conduit 138 in the target vessel, the device 130 removed, and one or more instruments passed through other ports to place the conduit in communication with a source of blood such as the aorta, a coronary vessel, or a heart chamber containing blood. Alternatively, the conduit could be placed in communication with the blood source prior to the target vessel.

The conduit may be placed in communication with the target vessel in any of several manners according to the invention. In the embodiment shown in FIGS. 6 and 6A, the lumen of the target vessel may be partially or completely occluded by the conduit (and in particular the liner) once the conduit section has expanded to its final position. As a result, native blood flow from a proximal source may be hindered or prevented from moving distally past the attachment site between the conduit and the target vessel. In the case of a coronary artery, the conduit could limit or block native blood flow through the artery, i.e., blood flowing through the artery from a proximal source, e.g., the aorta. Many patients undergoing a CABG procedure will have some native blood flow in one or more obstructed arteries. It therefore would be desirable to place a conduit in fluid communication with the target vessel in a manner that preserves such native blood flow in the target vessel.

According to another embodiment of the invention a conduit is placed in fluid communication with a target vessel while preserving native blood flow through the target vessel. That is, blood flowing through the target vessel prior to placing the conduit is free to flow past the site of the attachment. One way of achieving this is by constructing the conduit to include a portion that is placed in the target vessel and allows flow past the attachment site. Another way to preserve native flow is by forming an opening in a solid wall of a conduit placed in the target vessel lumen.

Figure 17:
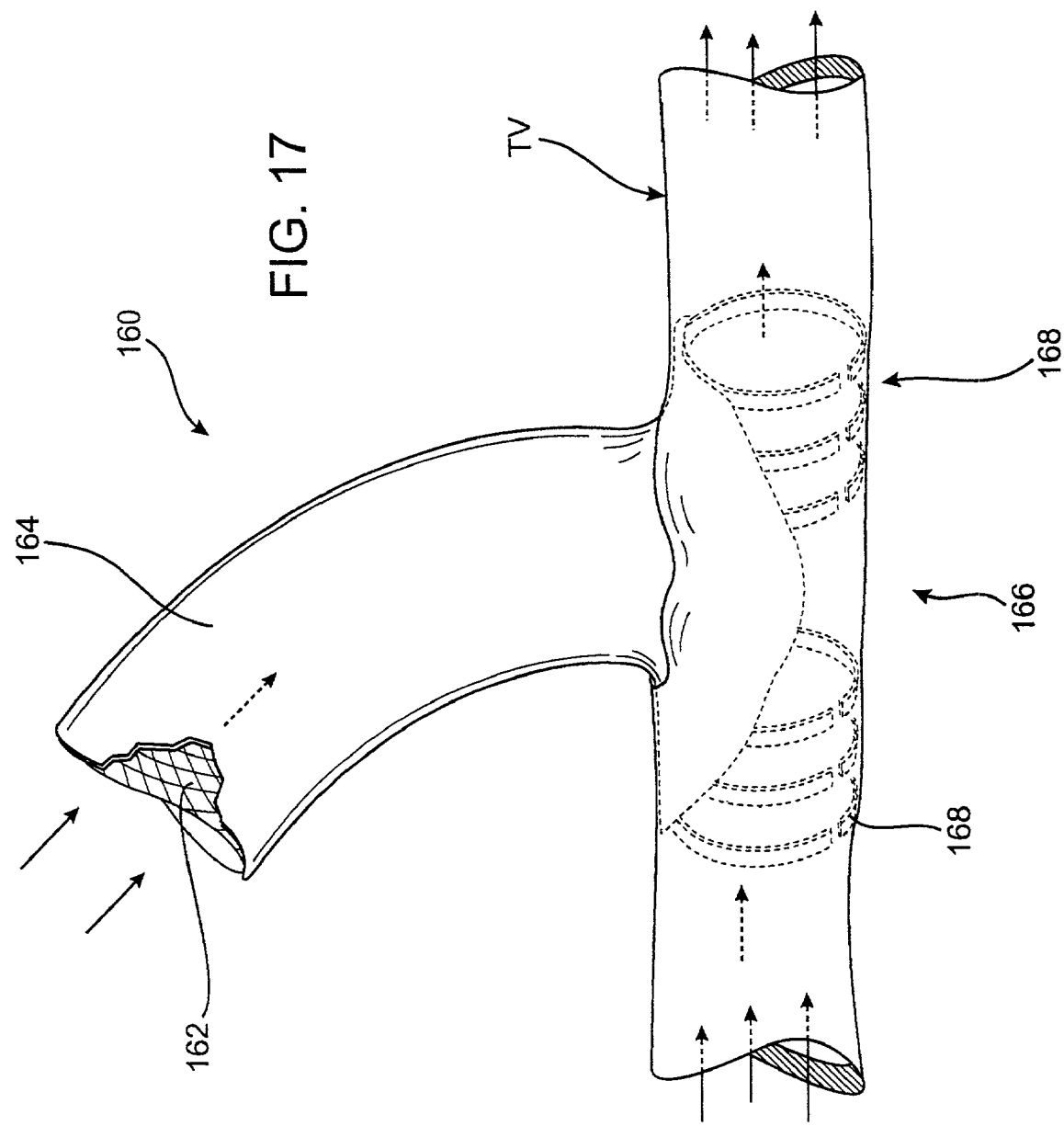
FIG. 17 is a perspective view of a conduit that has been placed in fluid communication with a target vessel according to another embodiment of the invention, wherein native flow through the target vessel is substantially preserved.

FIG. 17 shows a conduit 160 constructed in a manner that preserves native blood flow in the target vessel. The conduit 160 comprises a stent 162 coupled to a liner 164 in a manner described above with respect to previous embodiments. The stent 162 includes a frame portion 166 with one or more members 168 that engage the wall of the target vessel TV to secure the conduit 160 to the vessel. The liner 164 preferably surrounds (either partially or completely) the frame portion 166 but does not obstruct the lumen of the target vessel TV. The conduit 160, and in particular the stent 162 and frame portion 166, may be constructed and deployed in a target vessel according to the teachings in the aforementioned application Ser. No. 09/232,103, filed on Jan. 15, 1999 and entitled "Methods and Devices for Forming Vascular Anastomoses," the entire subject matter of which has been incorporated herein by reference.

Figure 18:
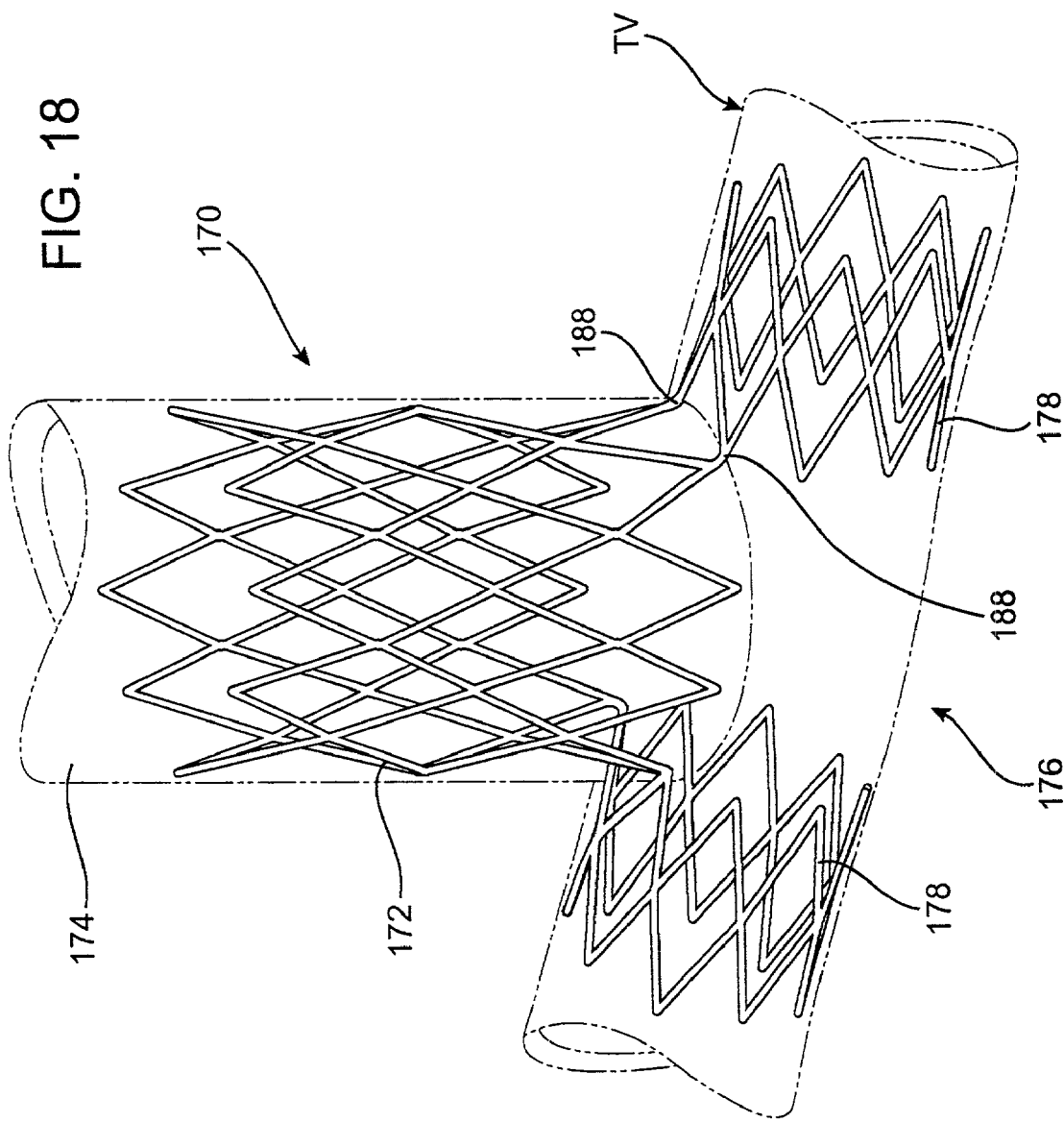
FIG. 18 is a perspective view of a conduit including a stent constructed according to another embodiment of the invention, wherein the stent places the conduit in fluid communication with a target vessel so as to substantially preserve native flow through the target vessel.

An alternative conduit embodiment that preserves native flow through the target vessel is designated by reference numeral 170 in FIG. 18 and comprises a stent 172 coupled to a liner 174, preferably in the manner described above with respect to previous embodiments. The stent 172 includes a frame portion 176 that includes a pair of frame members 178 which engage the wall of the target vessel TV to secure the conduit 170 to the vessel. The liner 174 preferably surrounds the frame portion 176 as described in connection with FIG. 17; however, for sake of clarity, the liner 174 is shown terminating at the junction of the conduit 170 and the target vessel TV.

Figure 19:
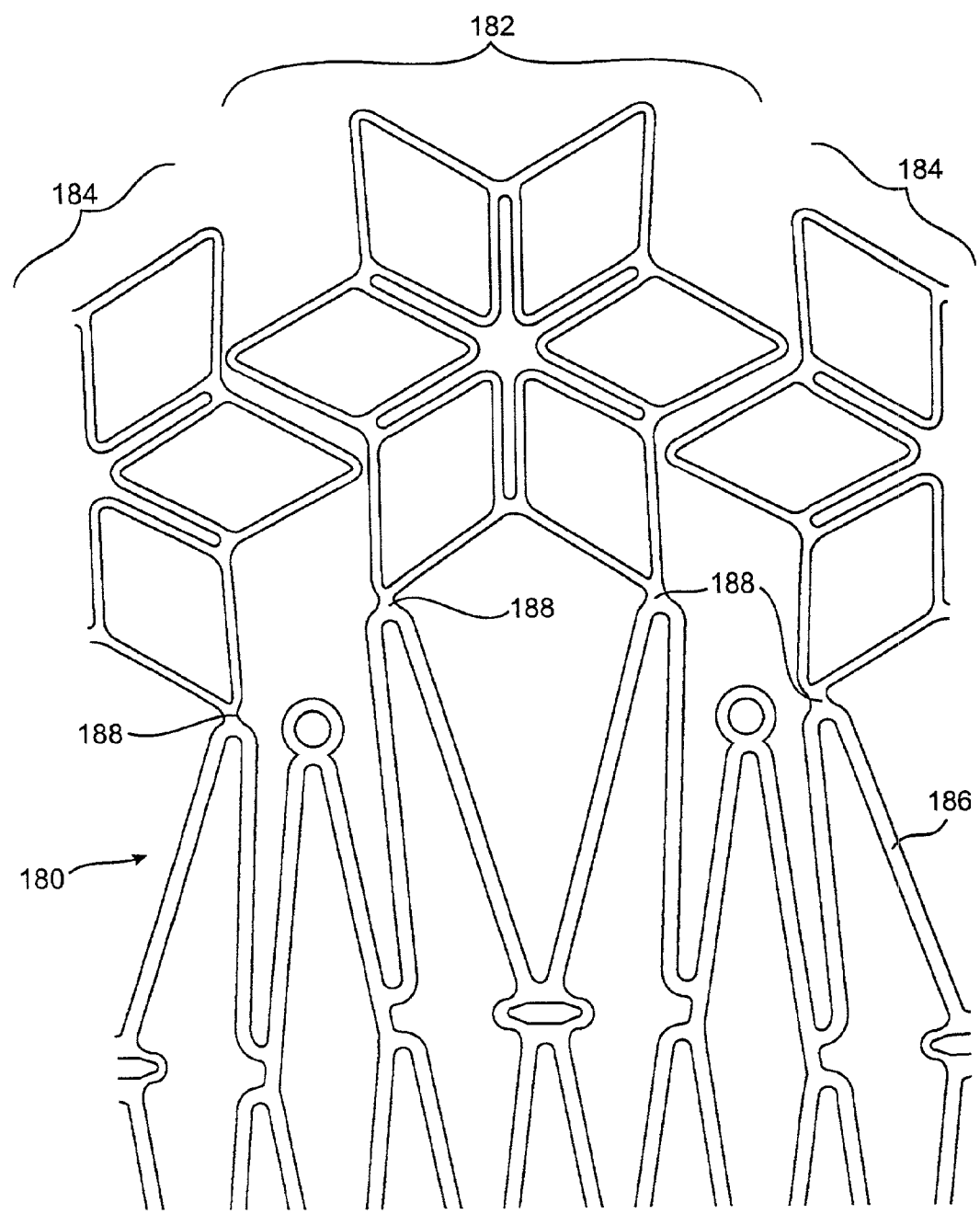
FIG. 19 is a flat pattern elevation view showing one end of the stent shown in FIG. 15.

FIG. 19 is a flat pattern (two-dimensional) illustration of a tube 180 that has been cut to form the stent 172 of FIG. 18. The tube is cut to form first and second sections 182, 184 corresponding to the respective frame members 178. The sections 182, 184 have a diamond-pattern construction and are joined to the body 186 by at least one, and preferably multiple attachment points 188. FIG. 19 shows the stent 172 in an expanded form but with the frame portions 176 disposed along a first axis which, in the illustrated embodiment, corresponds to the longitudinal axis of the stent body 186. The frame members 178 preferably move to the position shown in FIG. 18 in which they are disposed along a second axis which is generally transverse to the first axis. In the illustrated embodiment, the second axis is substantially perpendicular to the first axis, although other configurations may be used. Upon deployment of the conduit 170 in the target vessel the frame members 178 preferably move along a curved path from the first axis to the second axis.

Figure 20:
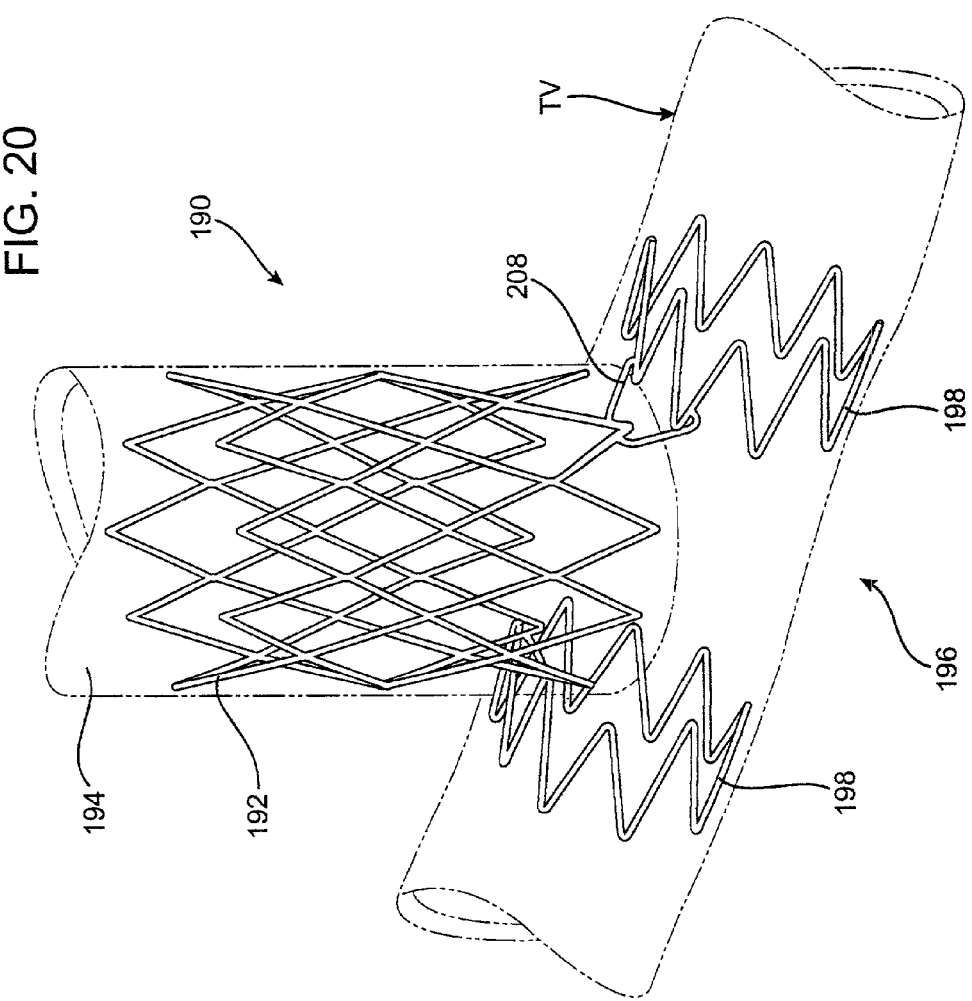
FIG. 20 is a perspective view of a conduit including a stent constructed according to another embodiment of the invention, wherein the stent places the conduit in fluid communication with a target vessel so as to substantially preserve native flow through the target vessel.

Another alternative conduit embodiment that preserves native flow through the target vessel is designated by reference numeral 190 in FIG. 20 and comprises a stent 192 coupled to a liner 194. The stent 192 and liner 194 may be coupled in the manner described above. The stent 192 includes a frame portion 196 which includes a pair of frame members 198 for engaging the wall of the target vessel TV, thereby securing the conduit 190 to the vessel as shown in FIG. 20. As in the embodiment of FIG. 18, the liner 194 preferably surrounds the frame portion 176 but, for sake of clarity, is shown ending at the junction of the conduit 170 and the target vessel TV.

Figure 21:
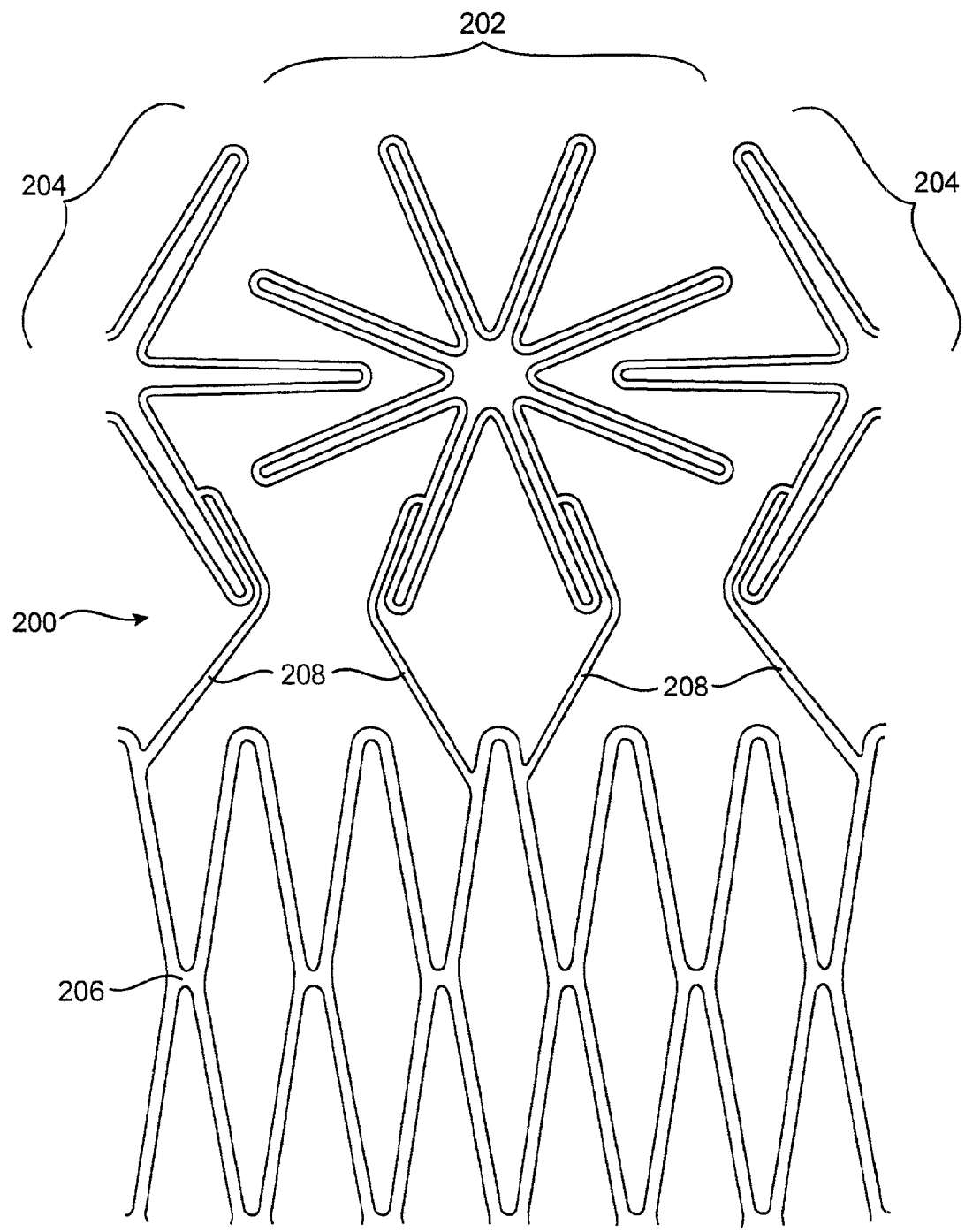
FIG. 21 is a flat pattern elevation view showing one end of the stent shown in FIG. 20.

FIG. 20 is a flat pattern (two-dimensional) illustration of a tube 200 that has been cut to form the stent 192 shown in FIG. 19. The tube is cut to form first and second sections 202, 204 corresponding to the respective frame members 198 which, in the illustrated embodiment, have a zigzag configuration. The sections 202 and 204 are joined to the stent body 206 by at least one, and preferably multiple attachment struts 208. FIG. 21 is similar to FIG. 19 in that it shows the stent 192 in an expanded form but with frame sections 198 disposed along the longitudinal axis of the stent body 186 instead of transverse to the body, which is the position the frame members 178 move to upon deployment of the conduit 190 in a target vessel.

The conduits depicted in FIGS. 17–21, and in particular the stents that form the vessel couplings of such conduits, may have various configurations and may be formed according to the process described above with respect to previous embodiments. That is, the stents 162, 172 and 192 may be cut or formed from a suitable material subjected to a procedure such as laser cutting, EDM (electrical discharge machining), photochemical etching, etc. The cut stent may be further processed or finished to remove burrs or surface irregularities, for example, by acid etching, electropolishing, or abrasive blasting. Next, the frame sections that engage the wall of the target vessel are shape-set to their expanded orientation. This may be done by placing the frame sections in that orientation and applying sufficient heat to produce a structure that will assume the desired configuration above a certain temperature, e.g., 5° below body temperature. The stent may then be placed in its collapsed orientation by cooling (e.g., with liquid nitrogen), coupled to a liner and loaded onto a delivery device, and then deployed in a target vessel.

The embodiments of the invention shown in FIGS. 17, 18 and 20 preserve native blood flow through the target vessel and have a construction that does not cover a major portion of the inner or posterior wall of the target vessel. As shown, the frame structure that is placed in the target vessel contacts the inner wall of the vessel to secure the conduit but leaves the majority of the vessel wall uncovered. This allows blood flowing through the target vessel to feed septal perforators (not shown but extending downward as viewed in FIG. 17) so as to perfuse the myocardial tissue. This feature thus prevents the myocardial tissue perfused by the septal perforators from becoming ischemic due to the conduit located in the target vessel. It should be appreciated that while it is preferred to leave the majority of the vessel wall unexposed to perfuse as many septal perforators as possible, the invention may be practiced with a conduit that covers more or less of the vessel wall than that shown.

The illustrated devices utilize a self-expanding stent and, as such, the device is not provided with an expansion mechanism for deploying the stent. It will be recognized, however, that either a self-expanding stent or a stent expanded by suitable means, e.g., a balloon or a non-inflatable expansion mechanism, may be used. For example, the device may be constructed the same as or similar to the device disclosed in application Ser. No. 09/232,102, filed on Jan. 15, 1999, and entitled "Methods and Devices for Forming Vascular Anastomoses," the entire subject matter of which has been incorporated herein by reference. The device could be provided with a separate inflation lumen for inflating the balloon to expand the stent, or the design in the aforementioned application may be used with seals such as O-rings or the like.

The invention also may use a conduit provided with a valve or other means for controlling or regulating blood flow. A valve could take the form, for example, of any of the valves disclosed in application Ser. No. 09/023,492, filed on Feb. 13, 1998, and entitled "Methods and Devices Providing Transmyocardial Blood Flow to the Arterial Vascular System of the Heart," the entire subject matter of which has been incorporated herein by reference.

Similarly, it will be appreciated that a conduit or vessel coupling configured to preserve native blood flow in a target vessel may be constructed differently than that shown in FIGS. 17–21. For example, the portion of the vessel coupling that is disposed in the target vessel could take the form of a single section of a coronary stent joined to the main body of the stent. Further, if desired the portion of the vessel coupling that permits native flow through the target vessel could control or meter the flow. Other variations may be used as well.

It will be appreciated that the features of the various preferred embodiments described herein may be used together or separately, while the illustrated methods and devices may be modified or combined in whole or in part. As an example, the attachment formed between the conduit and the target vessel may be suture-free while allowing or blocking native flow through the target vessel; alternatively, the attachment may be formed to allow native flow through the target vessel but be created using, in whole or in part, conventional suturing techniques.

It should be appreciated that a device constructed according to the invention could be operated with one or two hands (and by one or more users), although a one-hand operable embodiment is specifically illustrated. Also, the device of the invention may include removable or detachable components, or could be constructed as a one-piece instrument with no separable components. The device may be formed as a disposable instrument, a reusable instrument capable of being sterilized, or a combination of disposable and reusable components.

Further, it will be understood that the embodiments may be used in various types of procedures, for example, an open surgical procedure including a median sternotomy, a minimally invasive procedure utilizing one or more relatively small access openings or ports, or an endovascular procedure using peripheral access sites. Also, endoscopes or thoracoscopes may be used for visualization if the procedure is performed through very small ports. The different embodiments may be used in beating heart procedures, stopped-heart procedures utilizing cardiopulmonary bypass (CPB), or procedures during which the heart is intermittently stopped and started. Finally, any suitable delivery device, instrument or catheter may be used in conjunction with the invention.

It also will be recognized that the invention is not limited to the illustrated applications, namely, placing a coronary vessel in fluid communication with a source of blood. For example, the invention may find application in treating peripheral arterial disease in the distal abdominal aorta including the infrarenal aorta and aortoiliac segment, aortofemoral, or carotid, and to treat disease in the iliac and renal artery lesions.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method for deploying a conduit in a target vessel, the method comprising steps of:
    (a) providing a conduit having a first end, a second end and a lumen, wherein the conduit is movable between deployed and non-deployed positions and at least a portion of the conduit is held in the non-deployed position by a retention member, the retention member comprises a sheath that overlies the non-deployed portion of the conduit, wherein the conduit comprises a stent and the deployed and non-deployed positions correspond, respectively, to expanded and collapsed orientations of the stent;
    (b) positioning at least the non-deployed portion of the conduit in a lumen of a target vessel;
    (c) moving the retention member in a first direction with respect to the conduit to move the non-deployed portion of the conduit to the deployed position, the retention member moving distally toward the target vessel; and
    (d) moving the retention member in a second direction that is substantially opposite the first direction to remove the retention member from the target vessel, the retention member moving proximally away from the target vessel, wherein the sheath is removed through the lumen of the deployed portion of the conduit; and coupling the sheath to a sheath removal mechanism and removing the sheath and the sheath removal mechanism from the target vessel.

2. The method of claim 1, wherein the sheath and the sheath removal mechanism are removed through the lumen of the conduit.

3. The method of claim 1, further comprising providing the sheath removal mechanism with a tapered portion that is coupled to the sheath and forms a smooth outer profile for removing the sheath.

4. The method of claim 1, wherein the portion of the conduit is secured to the target vessel without using suture to form a substantially suture-free anastomosis.

5. A method for placing a conduit in fluid communication with a target vessel so as to preserve native flow through the target vessel, the method comprising steps of:
    (a) providing a vessel coupling and a conduit, wherein the vessel coupling has a first portion configured to secure the conduit to a target vessel so that the conduit is in fluid communication with the target vessel;
    (b) moving the vessel coupling generally along a first direction to place the first portion of the vessel coupling at least partially within the lumen of the target vessel; and
    (c) moving the first portion of the vessel coupling generally along a second direction within the lumen of the target vessel to deploy the vessel coupling and secure the conduit to the target vessel, wherein the second direction is transverse to the first direction.

6. The method of claim 5, wherein the first direction corresponds to the longitudinal axis of the conduit and the second direction corresponds to the longitudinal axis of the target vessel, and step (c) is performed by moving the first portion of the vessel coupling along a curved path between the two axes.

* * * * *